(12) United States Patent
Guelow et al.

(10) Patent No.: US 8,563,500 B2
(45) Date of Patent: Oct. 22, 2013

(54) METHODS AND COMPOUNDS FOR TREATING DISEASES CAUSED BY REACTIVE OXYGEN SPECIES

(75) Inventors: Karsten Guelow, Heidelberg (DE); Marcin Kaminski, Dossenheim (DE); Michael Kiessling, Dossenheim (DE); Peter H. Krammer, Heidelberg (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 449 days.

(21) Appl. No.: 12/676,617

(22) PCT Filed: Sep. 5, 2007

(86) PCT No.: PCT/EP2007/007754
§ 371 (c)(1),
(2), (4) Date: Mar. 5, 2010

(87) PCT Pub. No.: WO2009/030257
PCT Pub. Date: Mar. 12, 2009

(65) Prior Publication Data
US 2010/0305187 A1    Dec. 2, 2010

(51) Int. Cl.
*A01N 61/00* (2006.01)
*A01N 43/04* (2006.01)
*C12Q 1/68* (2006.01)
*C12N 15/63* (2006.01)
*C07H 21/04* (2006.01)

(52) U.S. Cl.
USPC ..... 514/1; 424/9.1; 424/9.2; 435/6; 435/91.1; 435/91.31; 435/455; 514/2; 514/44; 536/23.1; 536/24.5

(58) Field of Classification Search
USPC ............ 435/6, 91.1, 91.31, 455; 514/1, 2, 44; 536/23.1, 24.5; 424/9.1, 9.2
See application file for complete search history.

(56) References Cited

U.S. PATENT DOCUMENTS

2007/0141154 A1*  6/2007  Li et al. .................. 424/472

FOREIGN PATENT DOCUMENTS

| CA | 2534067 A1 | | 2/2005 |
| EP | 1561472 A | | 8/2005 |
| WO | WO 98/36748 | * | 8/1998 |
| WO | 00/66102 A | | 11/2000 |
| WO | WO 2004/017959 | * | 3/2004 |

OTHER PUBLICATIONS

Batandier et al., J. Bioenerg. Biomembr., vol. 38, pp. 33-42 (2006).*
Kaminski et al, Molecular & Cell. Biol., vol. 27, No. 10, pp. 3625-3639 (2007).*
Batandier et al., J. Bioeng. Biomembr., vol. 38, pp. 33-42 (2006).*
Brand et al., Free Radical Biology and Medicine, vol. 37, No. 6, pp. 755-767 (2004).*

* cited by examiner

*Primary Examiner* — Jane Zara
(74) *Attorney, Agent, or Firm* — Rothwell, Figg, Ernst & Manbeck, P.C.

(57) ABSTRACT

Provided is a method of treating a patient having an inflammatory disease by using a compound which inhibits the complex I-mediated ROS production, a medicament containing such compound and methods for screening for such compounds.

9 Claims, 18 Drawing Sheets

A

B

C

METHODS AND COMPOUNDS FOR TREATING DISEASES CAUSED BY REACTIVE OXYGEN SPECIES

CROSS REFERENCE TO RELATED APPLICATION

This application is a 35 U.S.C. 371 National Phase Entry Application from PCT/EP2007/007754, filed Sep. 5, 2007.

The present invention refers to a method for treating diseases, in particular immune diseases dependent on the CD95/CD95L signal system, by inhibiting the generation of reactive oxygen species (ROS).

INTRODUCTION

Under physiological conditions, reactive oxygen species (ROS) form as a natural byproduct of the normal metabolism of oxygen and have important roles in cell signaling. They are generally very small molecules and are highly reactive due to the presence of unpaired valence shell electrons. ROS include oxygen ions, free radicals and peroxides both inorganic and organic. During times of environmental stress, ROS levels can increase dramatically, which can result in significant damage to cell structures, resulting in a pathological condition known as oxidative stress. Cells are normally able to defend themselves against ROS damage through the use of enzymes such as superoxide dismutases (SOD) and catalases. Small molecule antioxidants such as ascorbic acid (vitamin C), uric acid, and glutathione also play important roles as cellular antioxidants. Similarly, polyphenol antioxidants assist in preventing ROS damage by scavenging free radicals. The effects of ROS on cell metabolism include not only roles in programmed cell death and apoptosis, but also positive effects such as the induction of host defense genes and mobilization of ion transport systems. In particular, platelets involved in wound repair and blood homeostasis release ROS to recruit additional platelets to sites of injury, providing a link to the adaptive immune system via the recruitment of leukocytes.

ROS are implicated in cellular activity to a variety of inflammatory responses including cardiovascular diseases. They may also be involved in hearing impairment via cochlear damage induced by elevated sound levels, ototoxicity of drugs such as cisplatin, and in congenital deafness in both animals and humans. Redox signaling is also implicated in mediation of apoptosis or programmed cell death and ischemic injury. Specific examples include stroke and heart attack.

Even though to date a clear connection can be drawn from an excess ROS production to certain immunological disorders resulting from intracellular signaling processes, the molecular source and the signalling steps necessary for ROS production are largely unknown. It is known in the art that ROS play a key role in regulation of Activation Induced T cell Death (AICD) by induction of CD95L expression. Since CD95L expression is crucial for induction of AICD, efforts have been made to explore the connection between T-cell receptor (TCR) signalling and regulation of CD95L transcription. Following TCR engagement the kinase ZAP70 is activated (11). ZAP70 phosphorylates the adaptor protein LAT (19) which recruits phospholipase C gamma 1 (PLCγ1) subsequently. The activation of PLCγ1 results in generation of inositol 3,4,5-triphosphate ($IP_3$) and diacylglycerol (DAG). $IP_3$ mediates an increase of cytosolic calcium ($Ca^{2+}$), whereas DAG activates PKC. The rise in cytosolic $Ca^{2+}$ causes activation of the transcription factor nuclear factor of activated T cells (NF-AT) (69), one of the key regulators of CD95L expression (41). In addition, ROS are shown to be crucial for activation-induced CD95L expression (7, 15, 25) possibly via the ROS inducible transcription factors NF-κB and AP-1 (17). Aerobic organisms produce ROS by several means; in mitochondria as by-product of respiration (63), at the endoplasmatic reticulum by cytochrome P450 (50), in the cytoplasm by xanthine oxidase (20), at the plasma membrane by NADPH oxidases (35, 46) and phospholipases (54), and in peroxisomes (56). Recently, the phagocytic NADPH oxidase (NOX2) has been shown to be one source for TCR-triggered ROS. However, NOX2 is not the only source for activation-induced ROS (30). Following T cell activation, respiratory activity increases (21) and mitochondrial ROS production may be enhanced (27). In addition, there are hints supporting a possible role of the mitochondrial electron transport chain (ETC) and cytochrome P450 as origins of activation-induced ROS (7).

Among others, WO2004017959 discloses treatment methods using aryl-substituted heterocyles which are capable of preventing ROS formation by inhibiting the so-called Fenton reaction, i.e. the reaction between hydroxide peroxide and reduced iron, by inhibiting the reduction of iron(III) to iron (II). Furthermore, WO9836748 describes the use of L-ergothioneine in preventing mitochondria from oxidative stress caused by enhanced ROS. However, none of the documents of the prior art provides methods and compounds that exert an inhibitory effect without hazarding the consequences of deleterious side effects when ROS production is, in principle, may be desired.

Consequently, there is a need for treatment methods and compounds which act precisely on the site of deleterious ROS production that gives rise to AICD via the CD95/CD95L signalling system, leading to a variety of diseases associated with the cells of the immune system, and, to directly and specifically inhibit the production of ROS.

The inventors of the instant invention have now surprisingly found that metformin, a compound which prevents mitochondrial complex I—mediated ROS production, can be used to inhibit the expression of the CD95 ligand and, as a consequence, also inhibits the phenomenon of AICD. Similar results were obtained when siRNA-mediated knockdown of the chaperone NDUFAF1, which is required for complex I assembly, was used for inhibition of complex I—mediated reverse electron flux. Thus, metformin or other inhibitors of complex I—mediated ROS production can be used as a pharmaceutical to treat diseases which are a result of an increased CD95/CD95 L signalling.

DETAILED DESCRIPTION

The problem of the prior art is solved by the present invention, which provides a method of treating a patient having a disease dependent on a dysfunction of the CD95/CD95L signal system, and a method of treating a patent having an inflammatory disease, the method comprising administering to said patient a therapeutically effective amount of a compound which inhibits complex I-mediated ROS production.

For the purpose of convenience, the term "compound which inhibits complex I-mediated ROS production" is hereinafter referred to as "complex I inhibitor".

As used herein, "reactive oxygen species" is synonym for oxygen radicals and hydrogen peroxide ($H_2O_2$), pro-oxidants and refers to molecules or ions formed by the incomplete one-electron reduction of oxygen. These reactive oxygen intermediates include singlet oxygen; superoxides; peroxides; hydroxyl radical; and hypochlorous acid. They contribute to the microbicidal activity of phagocytes, regulation of signal transduction and gene expression, and the oxidative damage to nucleic acids; proteins; and lipids. Preferably, the ROS the production of which shall be inhibited is hydrogen peroxide.

As used herein, "complex I" refers to an enzyme complex, also known as NADH—ubiquinone oxidoreductase (EC 1.6.5.3). The enzyme couples the transfer of two electrons from NADH to ubiquinone to the translocation of four protons across the mitochondrial inner membrane. The thus generated proton gradient is used by complex V to produce ATP. Mammalian complex I consists of 46 polypeptide subunits, seven encoded by the mitochondrial DNA and the remainder by the nuclear genome, a non-covalently bound flavomononucleotide (FMN) group and eight iron sulphur.

As used herein, "inhibiting complex I" means inhibiting, decreasing or abolishing the complex-I mediated process of electron transfer. The term "electron transfer" is synonym for "electron flux". Encompassed herein is the forward electron flux as well as the reverse electron flux. Because it can be envisaged that inhibiting the forward electron flux may be accompanied by undesired side effects, the use of a compound that inhibits the reverse electron flux is generally preferred.

An assay of how to measure reverse electron flux and the successful inhibition thereof, respectively, is described in Batandier et al. (Journal of Bioenergetics and Biomembranes, 2006, vol. 38, Nr. 1, pp. 33-42), which is incorporated herein by reference. Other examples include Hinkle et al., Journal of Biological Chemistry, 1967, Vol. 242, page 5169; or Grivennikova and Vinogradov, Biochimica et Biophysica Acta 1757 (2006) 553-561.

General complex I inhibitors that may be employed for the method of the present invention include, e.g., rotenone, piericidin A, ubicidin-3, rollinisatatin-1 and 2 (bullatacin), capsaicin, annonaceous acetogenins, pyridaben, fenpyroximate, fenazaquin, tebufenpyrad, substituted quinolones and quinolines, synthetically simplified deguelin compounds, antimycin A (AntA), myxothiazol (Myx), and hybrid structures of complex-I and complex-III inhibitors ("chromone derivatives"); acetogenines such as annonacin, and biguanides, such as phenformin, buformin and metformin.

Most preferably, the complex I inhibitor that may be employed for the method of the present invention is metformin.

The metformin which can be employed to enable the teaching of the present invention is well-described in the art. As used herein, the term "metformin" means metformin base or any pharmaceutically acceptable salt e.g., metformin hydrochloride and dibasic salts such as metformin fumarate and metformin succinate, originally described in U.S. Pat. No. 3,174,901. Commonly used is metformin as different salts thereof, mostly as hydrochloride salt. Also included is an acetylsalicyl acid salt or clofibrate salt as described in U.S. Pat. No. 3,957,853 and U.S. Pat. No. 4,080,472, which are incorporated herein by reference. Metformin is approved and commonly known as a pharmaceutical to treat non-insulin-dependent diabetes mellitus (NIDDM, type II diabetes). It is available under its trade name Glucophage® by Bristol Myers Squibb (see for example for reference US2007141154). Also encompassed for the method of the present invention are formulations described in US2007160671, which is incorporated by reference herein as well.

In another embodiment of the present invention, the inhibition of complex I can be achieved by destabilizing complex I as a whole, i.e. the complex of 46 subunits, or by destabilizing single subunits thereof. Preferably, the destabilization method affects the complex as a whole. It is known in the art that large protein complexes, like complex I, are kept in its conformational folding state by the aid of so-called chaperones. Chaperones are proteins that assist the non-covalent folding/unfolding and the assembly/disassembly of macromolecular structures, but do not occur in these structures when the latter are performing their normal biological functions. Human mitochondrial complex I assembly is mediated by NDUFAF1 (NADH dehydrogenase (ubiquinone) 1 alpha subcomplex, assembly factor 1) (see reference no. 66). Thus, complex I destabilization is preferably achieved by using siRNA for the purpose of interfering with/down-regulating the expression of NDUFAF1, leaving other, rather pan-acting chaperones unaffected.

As used herein, the term "treating" or "treatment" as used in relation to the treatment of diseases, particularly inflammatory diseases is to be understood as embracing both symptomatic and prophylactic modes, that is the immediate treatment, e.g. of acute inflammation (symptomatic treatment) as well as advance treatment to prevent, ameliorate or restrict long term symptomatology (prophylactic treatment). The term "treatment" as used in the present specification and claims in relation to such diseases is to be interpreted accordingly as including both symptomatic and prophylactic treatment, e.g., in the case of asthma, symptomatic treatment to ameliorate acute inflammatory events and prophylactic treatment to inhibit ongoing inflammatory status and to ameliorate future bronchial exacerbation associated therewith.

As used herein, the term "inflammatory disease" refers to diseases which are a result of an individual's reaction of connecting tissue and blood vessels to an external or internal inflammation stimulus, with the purpose to eliminate or inactivate said stimulus. Inflammation triggering effectors may include mechanical stimuli, or other physical factors, e.g. ionizing radiation, UV light, heat, coldness; chemical substances, e.g. bases, acids, heavy metals, bacterial toxins, allergens, and immune complexes, as well as pathogens, e.g. microorganisms and viruses, worms and insects; and pathogenic metabolism products, malfunctioning enzymes, malign tumors.

In a particular embodiment, the term "inflammatory disease" refers to a disease that results from a activation-dependent expression of CD95 and/or CD95 ligand (CD95L). In a further embodiment, the term "inflammatory disease" refers to a disease resulting from an increased expression of cytokines such as IL-2, IL-4, or TNF-alpha. It has been shown by the inventors of the present invention that the expression of either CD95L or the cytokines described above can be reduced by inhibiting complex I-mediated ROS production with metformin or other complex I inhibitors.

As used herein, "therapeutically effective amount" of the complex I inhibitor means a sufficient amount of said compound to treat a particular disease, at a reasonable benefit/risk ratio. In general, the term "therapeutically effective amount" shall refer to an amount of said compound which is physiologically significant and improves an individual's health. An agent, i.e. said compound, is physiologically significant if its presence results in a change in the physiology of the recipient human. For example, in the treatment of a pathological condition, administration of said compound which relieves or arrests further progress of the condition would be considered both physiologically significant and therapeutically effective. Said compound may be employed in pure form or, where such forms exist, in "pharmaceutically acceptable salt", ester or prodrug forms.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977), which is incorporated herein by reference. The salts can be prepared in situ during the final isolation and purification of the complex I inhibitors, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, berate, butyrate, camphorate, camphorsulfonate, citrate, cyclopentanepropionate, digluconate, dodecylsulfate, ethanesulfonate, formate, fumarate, glucoheptanoate, glycerophosphate, gluconate, hemisulfate, heptanoate, hexanoate, hydroiodide, 2-hydmxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate. 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl sulfonate and aryl sulfonate.

As described supra, the complex I inhibitors are useful in the treatment of inflammatory diseases, particularly inflammatory diseases which may arise due to an increased ROS production in response to an external or internal inflammation stimulus, which in turn leads to an increased expression of CD95L as well as cytokine such as 11-2, IL 4, TNF-alpha. Such inflammatory diseases can be subdivided into chronic inflammatory diseases, acute inflammatory diseases, allergic inflammatory disorders, graft-versus-host rejection diseases, and autoimmune disorders, all of which are encompassed within the present invention. Among these subgroups, inflammatory diseases of the respiratory tract, inflammatory skin diseases, allergic inflammatory disorders, inflammatory diseases of the gastrointestinal tract and inflammatory heart diseases can occur.

Accordingly, complex I inhibitors are useful for the treatment of diseases or conditions responsive to or requiring anti-inflammatory, immunosuppressive or related therapy, including topical administration for the treatment of such diseases or conditions of the eye, nasal passages, buccal cavity, skin, heart, colon or, especially, airways or lung. In particular complex I inhibitors permit topical anti-inflammatory, immunosuppressive or related therapy with the concomitant avoidance or reduction of undesirable systemic side effects, for example renal toxicity or general systemic immunosuppression.

Complex I inhibitors are particularly useful for the treatment of diseases and conditions of the airways or lung, i.e diseases of the respiratory tract, in particular inflammatory or obstructive airways disease. They are especially useful for the treatment of diseases or conditions of the airways or lung associated with or characterized by inflammatory cell infiltration or other inflammatory event accompanied by the accumulation of inflammatory cells, e.g. eosinophils and/or neutrophils.

In this respect, Complex I inhibitors are useful in the treatment of asthma of whatever type of genesis including both intrinsic and, especially, extrinsic asthma. They are useful for the treatment of atopic and non-atopic asthma, including allergic asthma, bronchitic asthma, exercise-induced asthma, occupational asthma, asthma induced following bacterial infection and other non-allergic asthmas. Complex I inhibitors are also useful for the treatment of bronchitis or for the treatment of chronic or acute airways obstruction associated therewith. Complex I inhibitors may be used for the treatment of bronchitis of whatever type or genesis, including, for example, acute bronchitis, arachidic bronchitis, catarrhal bronchitis, chronic bronchitis, croupous bronchitis, phthinoid bronchitis and so forth. Complex I inhibitors are in addition useful for the treatment of pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, berylliosis, chalicosis, ptilosis, siderosis, silicosis, tabacosis and, in particular, byssinosis. Complex I inhibitors may also be used to treat any disease or condition of the airways or lung requiring immunosuppressive therapy, e.g., for the treatment of autoimmune diseases of, or as they affect, the lungs (for example, for the treatment of sarcoidosis, alveolitis or chronic hypersensitivity pneumonitis) or for the maintainance of allogenic lung transplant, e.g., following lung or heart lung transplantation.

For the above purposes, some complex I inhibitors preferably will be administered topically within the airways, e.g. by the pulmonary route, by inhalation. While having potent efficacy when administered topically, complex I inhibitors are devoid of, or exhibit relatively reduced, systemic activity, e.g. following oral administration. Complex I inhibitors thus provide a means for the treatment of diseases and conditions of the airways or lung with the avoidance of unwanted systemic side effect, e.g., consequent to inadvertent swallowing of drug substance during inhalation therapy. (It is estimated that during the course of maneuvers required to effect administration by inhalation, up to 90% or more of total drug substance administered will inadvertently be swallowed rather than inhaled). By the provision of complex I inhibitors which are topically active, e.g. effective when inhaled but systemically inactive, the present invention makes complex I inhibitor therapy available to subjects for whom such therapy might otherwise be excluded, e.g., due to the risk of systemic, in particular immunosuppressive, side effects.

Complex I inhibitors are also useful for the treatment of other diseases or conditions, in particular diseases or conditions having an autoimmune or inflammatory component and for which topical therapy may be practiced, for example, treatment of diseases and conditions of the eye such as conjunctivitis, keratoconjunctivitis sicca, and vernal conjunctivitis and maintenance of corneal transplant, diseases affecting the nose including allergic rhinitis, diseases and conditions of the skin including psoriasis, atopic dermatitis, pemphigus and contact dermatitis, as well as diseases of the colon, for example Crohn's disease and ulcerative colitis.

As immunosuppressants, complex I inhibitors are useful when administered for the prevention of immune-mediated tissue or organ graft rejection. Examples of transplanted tissues and organs which suffer from these effects are heart, kidney, liver, medulla ossium, skin, cornea, lung, pancreas, intestinum tenue, limb, muscle, nervus, duodenum, small-bowel, pancreatic-islet-cell, and the like; as well as graft-versus-host diseases brought about by medulla ossium transplantation.

The regulation of the immune response by complex I inhibitors would also find utility in the treatment of autoimmune disorders, such as rheumatoid arthritis, systemic lupus erythematosis, hyperimmunoglobulin E, Hashimoto's thyroiditis, multiple sclerosis, progressive systemic sclerosis, myasthenia gravis, type I diabetes, uveitis, allergic encephalomyelitis, glomerulonephritis, and the like; and further infectious diseases caused by pathogenic microorganisms, such as HIV. In the particular cases of HIV-1, HIV-2 and related retroviral strains, inhibition of T-cell mitosis would suppress the replication of the virus, since the virus relies upon the host T-cell's proliferative functions to replicate.

Further uses include the treatment and prophylaxis of inflammatory and hyperproliferative skin diseases and cutaneous manifestations of immunologically-mediated illnesses, such as psoriasis, atopical dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, keratitis, herpetic keratitis, conical cornea, dystrophia epithelialis comeae, corneal leukoma, ocular pemphigus, Mooren's ulcer, Scleritis, Graves' opthalmopathy, Vogt-Koyanagi-Harada syndrome, sarcoidosis, multiple myeloma, etc.; inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury can be treated or prevented by complex I inhibitors.

Other treatable conditions would include but are not limited to Parkinson's disease, ischemic bowel diseases, inflammatory bowel diseases, necrotizing enterocolitis, intestinal lesions associated with thermal burns; intestinal inflammations/allergies such as Coeliac diseases, proctitis, eosinophilic gastroenteritis, and mastocytosis; food-related allergic diseases which have symptomatic manifestation remote from the gastrointestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infarction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine release; Behcet's disease such as intestinal-, vasculo- or neuro-Behcet's disease, and also Behcet's which affects the oral cavity, skin, eye, vulva, articulation, epididymis, lung, kidney and so on.

Furthermore, the complex I inhibitors may be used for the treatment of neurological disorders and injuries, particularly central nervous system injuries e.g. brain injuries and/or spinal cord injuries as described in WO2004/71528 which is herein incorporated by reference.

Aqueous liquid compositions of the present invention may be particularly useful for the treatment and prevention of various diseases of the eye such as autoimmune diseases (including, for example, conical cornea, keratitis, dysophia epithelialis corneae, leukoma, Mooren's ulcer, sclevitis and Graves' ophthalmopathy) and rejection of corneal transplantation. In particular, compositions pertaining to the present invention are useful for treating a subject for immune-mediated organ or tissue allograft rejection, a graft-versus-host disease, an autoimmune disease, an obstructive airway disease, a hyperproliferative disease, or an ischemic or inflammatory intestinal or bowel disease.

Accordingly, the present invention further refers to pharmaceutical preparations for the treatment of inflammatory diseases which comprises a complex I inhibitor and, optionally, a pharmaceutically acceptable carrier, and methods for preparing such pharmaceutical compositions. The methods for preparing pharmaceutical compositions, i.e. medicaments, are known per se to the skilled artisan.

The specific therapeutically-effective dose level for any particular patient will depend upon a variety of factors including the disorder being treated and the severity of the disorder; activity of the specific complex I inhibitor employed; the specific composition employed; the age, body weight, general health, sex and diet of the patient; the time of administration, route of administration, and rate of excretion of the specific complex I inhibitor employed; the duration of the treatment; drugs used in combination or coincidental with the specific complex I inhibitor employed; and like factors well known in the medical arts. For example, it is well within the skill of the art to start doses of the complex I inhibitor at levels lower than required to achieve the desired therapeutic effect and to gradually increase the dosage until the desired effect is achieved.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, phosphate buffer solutions; non-toxic, compatible lubricants such as sodium lauryl sulfate and magnesium stearate; as well as coloring agents, releasing agents, coating agents, sweetening, flavoring and perfuming agents. Preservatives and antioxidants can also be present in the composition, according to the judgment of the formulator.

The compositions may be administered to humans and other animals orally, rectally, parenterally, intracisternally, intravaginally, intraperitoneally, topically (as by powders, ointments, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion.

Dosage forms for topical or transdermal administration of complex I inhibitors include ointments, pastes, creams, lotions, gels, plasters, cataplasms, powders, solutions, sprays, inhalants or patches. The active component, i.e. the complex I inhibitor, is admixed under sterile conditions with a pharmaceutically acceptable carrier and any needed preservatives or buffers as may be required. The ointments, pastes, creams and gels may contain, in addition to an active complex I inhibitor of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to complex I inhibitors, excipients such as lactose, talc, silicic acid, aluminum hydroxide, calcium silicates and polyamide powder, or mixtures of these substances. Sprays can additionally contain customary propellants such as chlorofluorohydrocarbons. For nasal administration, complex I inhibitors will suitably be administered in liquid or powdered form from a nasal applicator. Forms suitable for ophthalmic use will include lotions, tinctures, gels, ointment and ophthalmic inserts, again as known in the art. For rectal administration, i.e., for topical therapy of the colon, complex I inhibitors may be administered in suppository or enema form, in particular in solution, e.g., in vegetable oil or like oily system for use as a retention enema.

It is clear that safety may be maximized by delivering the drugs by the inhaled route either in nebuliser form or as dry powder. Clearly the great advantage of the inhaled route, over the systemic route, in the treatment of asthma and other diseases of airflow obstruction and/or of chronic sinusititis, is that patients are exposed to very small quantities of the drug and the complex I inhibitor is delivered directly to the site of action.

Complex I inhibitors therefore are preferably employed in any dosage form appropriate for topical administration to the desired site. Thus, for the treatment of diseases of the airways or lungs, complex I inhibitors may be administered via the pulmonary route/by inhalation from an appropriate dispenser device. For this purpose, complex I inhibitors may be employed in any suitable finely dispersed or finely dispersible form, capable of administration into the airways or lungs, for example in finely divided dry particulate form or in dispersion or solution in any appropriate (i.e., pulmonarily administerable) solid or liquid carrier medium. For administration in dry particulate form, complex I inhibitors may, for example, be employed as such, i.e., in micronised form without any additive materials, in dilution with other appropriate finely divided inert solid carrier or diluent (e.g., glucose, lactose, mannitol, sorbitol, ribose, mannose or xylose), in coated particulate form or in any other appropriate form as known in the art for the pulmonary administration of finely divided solids. Pulmonary administration may be effected using any appropriate system as known in the art for delivering drug substance in dry or liquid form by inhalation, e.g. an atomizer, nebulizer, dry-powder inhaler or like device. Preferably a metered delivery device, i.e., capable of delivering a predetermined amount of complex I inhibitor at each actuation, will be employed. Such devices are known in the art.

Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminium monostearate and gelatine.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations may be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active complex I inhibitor is mixed with at least one inert, pharmaceutically-acceptable excipient or carrier, such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules may be prepared with coatings and shells such as enteric coatings and other coatings well known in the pharmaceutical formulating art, They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Liquid dosage forms for oral administration include pharmaceutically-acceptable emulsions, solutions, suspensions, syrups and elixirs. In addition to the active complex I inhibitors, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Suspensions may contain, in addition to the active complex I inhibitors, suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically-acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers. Alternatively, the composition may be pressurized and contain a compressed gas, such as nitrogen or a liquified gas propellant. The liquified propellant medium and indeed the total composition are preferably such that the active ingredient does not dissolve therein to any substantial extent. The pressurized composition may also contain a surface-active agent, such as a liquid or solid non-ionic surface-active agent or may be a solid anionic surface-active agent. It is preferred to use the solid anionic surface-active agent in the form of a sodium salt.

A further form of topical administration is to the eye, as for the treatment of immune-mediated conditions of the eye such as autoimmune diseases, allergic or inflammatory conditions, and corneal transplants. The complex I inhibitor is delivered in a pharmaceutically acceptable ophthalmic vehicle, such that the complex I inhibitor is maintained in contact with the ocular surface for a sufficient time period to allow the complex I inhibitor to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Complex I inhibitors may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming Liposomes can be used. The present compositions in liposome form can contain, in addition to a complex I inhibitor, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Another object of the present invention refers to a method of screening for a compound which inhibits complex I-mediated ROS production, the method comprising
  (a) contacting cells, particularly T-cells, with the compound under investigation,
  (b) staining said cells with an oxidation-sensitive dye, and
  (c) measuring the intensity of said dye
wherein a decreasing intensity as compared to cells that are not contacted with said compound is indicative of an inhibitory effect of said compound.

Dyes that are sensitive to oxidation, i.e. can be used to determine ROS production, and as a result, change their intensity are well-known in the art. In principle, all dyes which change their intensity upon an oxidation shift can be used for the method of the instant invention. In a preferred embodiment, the dye to be used for the determination of oxygen species is fluorescently labelled.

Examples of such dyes include, among others, Carboxy-$H_2$DCFDA, Milobox, CM-$H_2$DCFDA, Dihydrocalcein AM, Dihydrorhodamine 123, Dihydrorhodamine 6G, $H_2$DCFDA, Lucigenin, Luminol, RedoxSensor Red CC-1,3'-(p-Aminophenyl) fluorescein, 3'-(p-Hydroxyphenyl) fluorescein, CM-$H_2$DCFDA, Proxyl fluorescamine, TEMPO-9-AC, BODIPY FL EDA, BODIPY 665/676, Carboxy-$H_2$DCFDA, DPPP, cis-Parinaric acid, Singlet Oxygen Sensor Green reagent, Coelenterazine, Dihydroethidium. Most preferably, $H_2$DCFDA is used as the dye.

If the dye is fluorescently labeled, the intensity is preferably measured by fluorescent-activated cell sorting (FACS) analysis or using a fluorometer.

Examples of how to perform the method of invention is described in Example 8 or in Guelow et al (Journal of Immunol. 2005 May 1; 174(9):5249-60).

As described supra in the present invention, the inflammatory diseases which may be treated by the use of complex I inhibitors, respectively the medicaments containing them, may arise due to an increased ROS production.

Therefore, the present invention further refers to a method of inhibiting ROS production within cells, the method comprising the step of treating said cells with a complex I inhibitor.

Figure 1:
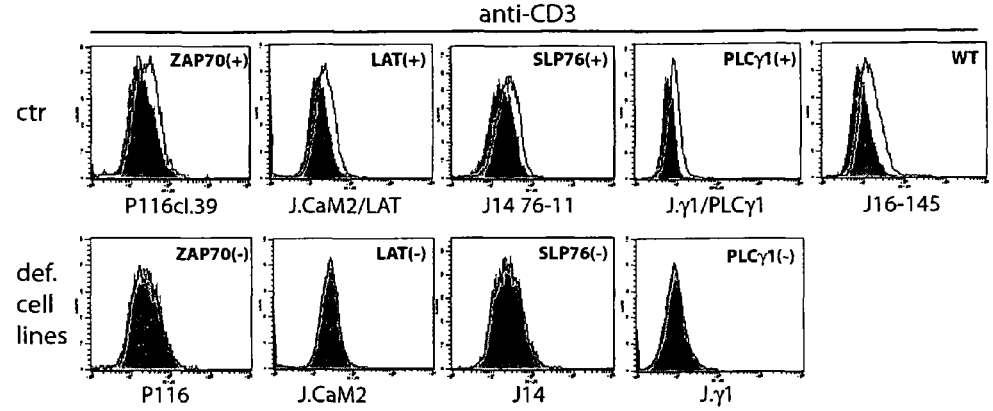
FIG. 1. Activation-induced ROS generation depends on the proximal TCR signalling machinery. A, B, Jurkat J16-145 cells, P116 (ZAP70 negative Jurkat cells), J.CaM2 (LAT negative Jurkat cells), J.CaM2/LAT (LAT-retransfected control cells), J14 (SLP76 deficient Jurkat cells), J14 76-11 (SLP76 retransfected control cells), J.γ1 (PLCγ1 deficient Jurkat cells) and J.γ1/PLCγ1 (PLCγ1-retransfected control cells) were stimulated via plate-bound anti-CD3 antibodies (A) or with PMA (B) for 30 min. Thereafter, cells were stained with DCFDA. Representative FACS profiles for activation-induced DCFDA oxidation are shown. C, Schematic diagram of TCR signalling.
Figure 1:
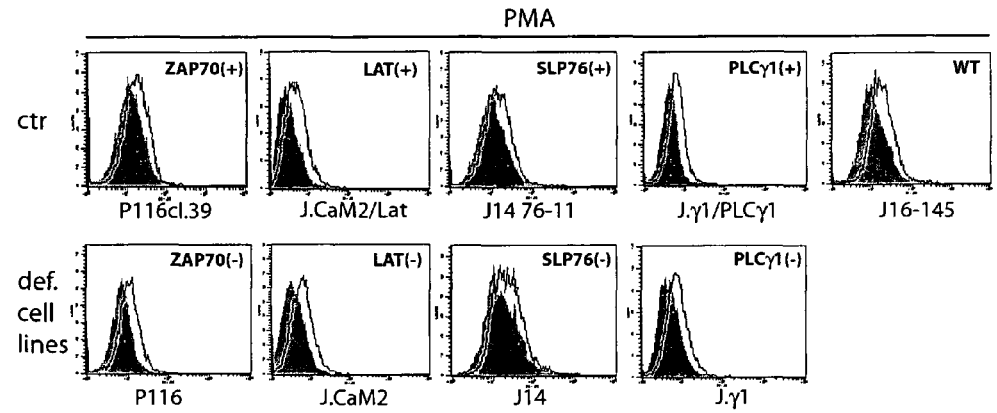
Figure 1:
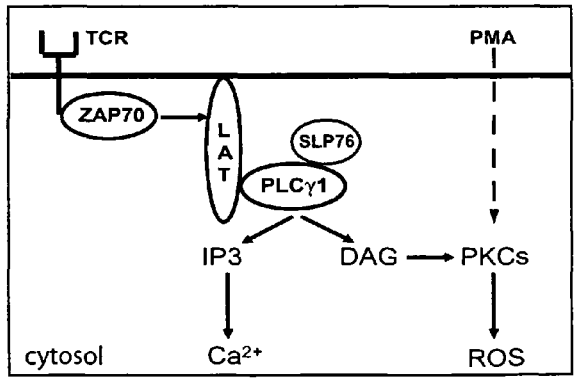

C, J16-145 Jurkat T cells were transfected with 75 nM of scrambled- (ctr) or NDUFAF1-siRNA oligonucleotides (oligonucleotides #1 and #2). After 72 h of resting, cells were treated with PMA/ionomycin for 1 h. Subsequently, RNA was isolated, reverse-transcribed, and amplified using IL-2, IL-4 and actin-specific primers.

D, Pre-activated (day "6") peripheral human T cells were pre-treated with indicated amounts of metformin for 1 h. Next, cells were stimulated with anti-CD3 antibodies for 1 h. Subsequently, RNA was isolated, reverse-transcribed, and amplified using TNF α and actin-specific primers.

The invention is further explained by the following examples without being bound to it.

EXAMPLES

Example 1

Chemicals. Dichlorodihydrofluorescein diacetate (DCFDA) was obtained from Molecular Probes, Germany. The cell permeable, myristoylated pseudosubstrate peptide inhibitors (general anti-PKC and anti-PKCθ) were purchased from Calbiochem, Germany. Primary antibodies against human PKCδ and PKCθ were supplied by BD Transduction Lab., Germany. Primary antibodies against human MnSOD and LAT were obtained from Upstate Biotech., USA. The primary antibody against human ZnCuSOD was purchased from Santa Cruz Biotech., Germany. The neutralising anti-CD95L antibody Nok1 was obtained from BD Pharmingen, Germany. All other chemicals and primary antibodies against human tubulin α were supplied by Sigma-Aldrich, Germany. The agonistic monoclonal antibody anti-Apo-1 (mouse IgG3) recognizing an extracellular part of CD95 (Apo1/Fas) (62) and the monoclonal anti-CD3 antibody OKT3 (25) were prepared as described.

Example 2

Cell culture. Jurkat J16-145 is a sub-clone of the human T lymphoblastoid cell line Jurkat J16 (25). J.CaM2 is a LAT negative Jurkat cell line and J.CaM2/LAT is the control cell line retransfected with LAT (19). P116 is a ZAP70 negative Jurkat cell line (68) and P116cl.39 is the retransfected control cell line. J14 is a SLP76 deficient cell line and J14 76-11 is the retransfected control cell line (37). J.γ1 is a PLCγ1 deficient Jurkat cell line and J.γ1/PLCγ1 is the retransfected control cell line (29). Jurkat cells were cultured in IMDM medium supplemented with 10% FCS.

Example 3

Generation of pseudo-$\rho^0$ cells. Cells depleted of mitochondrial DNA (mtDNA) were generated as described previously (12, 36) with minor modifications. Briefly, Jurkat J16-145 cells were cultured in IMDM medium supplemented with ethidium bromide (250 ng/ml) for up to 21 days. Ethidium bromide accumulates in much higher concentrations in the mitochondrial matrix than in the nucleus. Therefore, it can be used to selectively inhibit mtDNA replication. The amount of mtDNA was examined by isolation of DNA followed by PCR specific for the mitochondrial origin of replication (ori-mt).

The amplified product spanned ori-mt of the mtDNA heavy strain between position 15868 and 754: sense 5'-GAAAA-CAAAATACTCAAATGGGCC-3' and antisense 5'-CCTTTTGATCGTGGTGATTTAGAGGG-3'. Cells depleted in mtDNA rely energetically mainly on glycolysis and have impaired nucleotide metabolism. Therefore, pseudo-$\rho^0$ cells were further cultured in IMDM medium supplemented with ethidium bromide (250 ng/ml), uridine (50 µg/ml), and sodium pyruvate (110 mg/ml). Since cells were not completely deficient in mtDND they will be referred as pseudo-$\rho^0$ cells (12). To reconstitute mtDNA content pseudo-$\rho^0$ cells were transferred to the standard medium. Cells recovered to normal phenotype in 21-23 days.

Example 4

Isolation of total cellular DNA. Jurkat J16-145 cells were lysed for 1 h at 55° C. in 0.2M sodium acetate, 6.25% SDS solution containing 250 µg/ml proteinase K. Genomic DNA was isolated by a phenol/chloroform-extraction.

Example 5

Isolation of human peripheral T cells. Human peripheral T cells were prepared by Ficoll-Plaque density centrifugation, followed by rosetting with 2-amino-ethylisothyo-uronium-bromide-treated sheep red blood cells as described (25). For activation, resting T cells were cultured at a concentration of $2 \times 10^6$ cells/ml with 1 µg/ml PHA for 16 h. Next, T cells were cultured in RPMI 1640 supplemented with 10% FCS and 25 U/ml IL-2 for 6 days (day 6 T cells) as described (25).

Example 6

Isolation of human polymorphonuclear cells. Neutrophils from healthy individuals were prepared by Polymorphprep® density centrifugation according to the manufacturer's instructions (Axis-Shield, Norway).

Example 7

Assessment of cell death. To induce CD95L expression and/or subsequent apoptosis, cells were stimulated with anti-CD3 antibody (OKT3, 30 µg/ml) or PMA (10 ng/ml) and ionomycin (1 µM). Cell death was assessed by a drop in the forward-to-side-scatter (FSC/SSC) profile in comparison to living cells and recalculated to "specific cell death" as described (25).

Example 8

Determination of anti-CD3 and PMA induced ROS generation. Jurkat cells were stimulated either with plate-bound anti-CD3 (OKT3, 30 µg/ml) or by PMA (10 ng/ml) for 30 min and stained with the oxidation-sensitive dye $H_2DCFDA$ (5 µM). Since activation-induced ROS generation in human T cells was maximal at 30 min stimulation (25) this time point was chosen for all experiments. Incubation was terminated by washing with ice-cold PBS. ROS generation was determined by FACS and quantified as "Increase in Mean Fluorescence Intensity (MFI)" [%], calculated according to the following formula: "Increase in MFI" $[\%] = [(MFI_{(stimulated)} - MFI_{(unstimulated)})/MFI_{(unstimulated)}] \times 100$ as described (15). Cells were preincubated with inhibitors for 5 min prior to stimulation with exception of anti-PKC peptide inhibitors (20 min) and metformin (1 h). All experiments were performed in triplicates. Results shown are representative of at least three independent experiments.

Example 9

ATP determination. Cells were lysed by freezing and thawing. Cellular ATP was measured according to manufacturer's instructions (ATP-determination Kit, Molecular Probes, Germany).

Example 10

Figure 4:
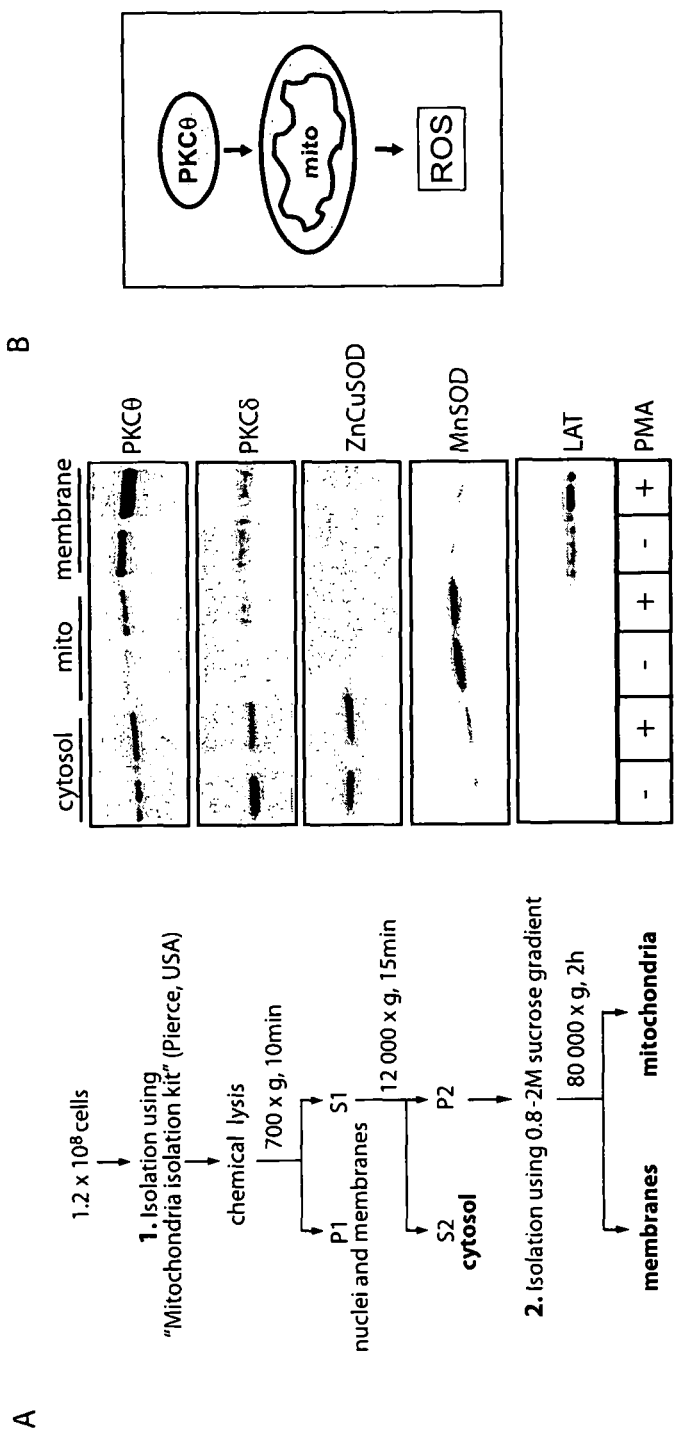
FIG. 4. PKCθ is translocated towards mitochondria upon PMA treatment. A, J16-145 cells were stimulated with PMA for 10 min. Cells were lysed and cellular fractions were separated as depicted in diagram (S1, S2—respective supernatants, P1, P2—respective pellets,). Highlighted fractions were separated by SDS-PAGE and analyzed by Western blot for content of PKCθ, PKCδ, ZnCuSOD (cytoplasmic marker), MnSOD (mitochondrial marker) and LAT (plasma membrane marker). B, Schematic diagram of PKCθ translocation and ROS induction. C-H, Involvement of mtDNA encoded proteins in activation-induced ROS generation and AICD. C, Total cellular DNA was isolated from parental J16-145 cells, J16-145 cells cultured in the presence of uridine (50 μg/ml) and pyruvate (110 mg/ml) (U+P) and J16-145 cells cultured in the presence of U+P and ethidium bromide (250 ng/ml) (ps-ρ$^0$). For PCR amplification of the origin of replication of mitochondrial heavy strand (mt-ori), 100 ng of DNA template was used (upper panel). Amplification of the β-actin gene fragment was used as a loading control (lower panel). D, Cells depleted of mtDNA show an impaired activation-induced ROS. Parental J16-145 cells cultured in medium supplemented with U+P (U+P) or cells depleted of mtDNA)(ps-ρ$^0$) were stimulated via plate-bound anti-CD3 antibodies (left panel) or with PMA (right panel) for 30 min, stained with DCFDA and analysed by FACS. The percentage of increase in MFI is shown. E, Cells depleted of mtDNA show lowered AICD. Cells (U+P) or (ps-ρ$^0$) as described in (C) were stimulated via plate-bound anti-CD3 antibodies or with PMA/ionomycin. After 24 h cell death was measured by a drop in FSC/SSC index and results were recalculated to "specific cell death". F, The content of mtDNA was tested for parental J16-145 cells (J16-145) or ps-ρ$^0$ cells, which regained mtDNA after long-term culture due to withdrawal of ethidium bromide from culture medium (recov.). Total cellular DNA (100 ng) was used and amplified as described in (C). G, Parental Jurkat J16-145 cells cultured in standard medium (J16-145) or ps-ρ$^0$ cells after recovery of mtDNA content (recov.) were stimulated by plate-bound anti-CD3 antibodies (left panel) or with PMA (right panel) for 30 min, activation-induced ROS production was measured as in (D). H, Parental J16-145 (J16-145) or (recov.) cells were stimulated by plate-bound anti-CD3 antibodies (left panel) or with PMA/ionomycin (right panel). After 24 h cell death was determined as described in (E).
Figure 4:
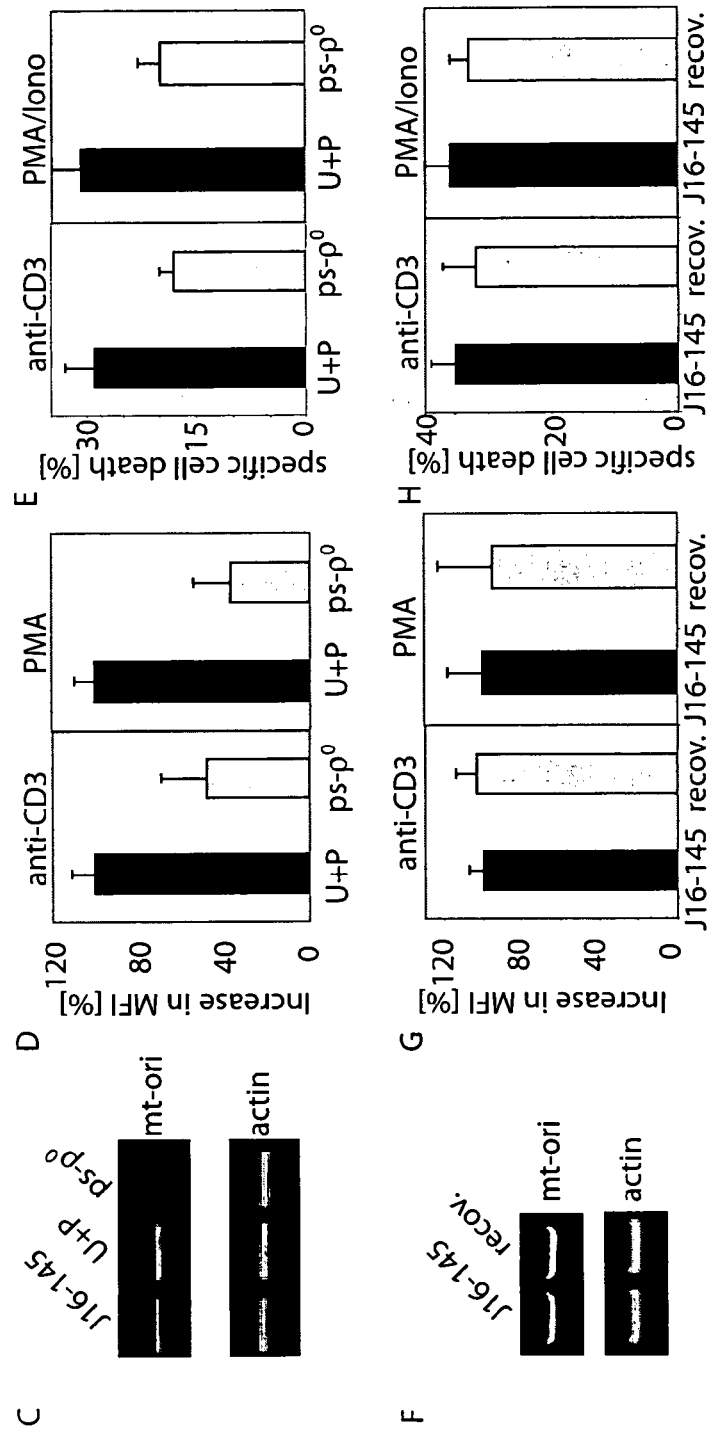

Mitochondria isolation and Western blot analysis. Crude mitochondrial fraction (containing membrane impurities) and cytoplasmic fraction were isolated using Mitochondria Isolation Kit (Pierce, USA) according to the manufacturer's instructions. Next, membranes were separated from mitochondria by isopycnic 0.8-2M sucrose gradient centrifugation for 2 h at 80 000 g. FIG. 4A shows schematic diagram of the purification procedure. Cells were lysed in RIPA lysis buffer [60 mM NaCl, 25 mM Tris/HCl, 0.5% desoxycholate, 1 mM DTT and Halt Protease Inhibitor Cocktail (Pierce, USA)] and protein concentration was measured by BCA assay (Pierce, USA). SDS-PAGE and Western blot analysis was performed as described (24). Western blots were quantified by standard scanning densitometry using the NIH Image program version 1.36b.

Example 11

RNA preparation and semi-quantitative RT-PCR. RNA was isolated using Trizol reagent (Invitrogen, Germany)

according to manufacturer's instructions. Total RNA (5 μg) was reverse-transcribed using a RT-PCR kit (Applied Biosystems, Germany). Aliquots were amplified by PCR as described (25). Primers for detection of CD95L, β-actin and NDUFAF1 were used as described (25, 40, 66). Primers used for amplification of MnSOD (SOD2) and Zn/CuSOD (SOD1) transcripts were: MnSOD, sense 5'-CTTCAGCCT-GCACTGAAGTTCAAT-3' antisense 5'-CTGAAGGTAG-TAAGCGTGCTCCC-3' and Zn/CuSOD, sense 5'-GCGAC-GAAGGCCGTGTGCGTGC-3' antisense 5'-CTAGAATTTGCGGTGGACGATGGAGGG-3'.

Example 12

Quantitative PCR. The primers and fluorescent-labeled probes used here were CD95L sense 5'-AAAGTGGC-CCATTTAACAGGC-3', antisense 5'-AAAGCAGGACAAT-TCCATAGGTG-3', probe 5'-TCCAACTCAAGGTCCAT-GCCTCTGG-3'; β-actin sense 5'-ACCCACACTGTGCCCATCTACGA-3', antisense 5'-CAGCGGAACCGCTCATTGCCAATGG-3', probe 5'-ATGCCCTCCCCCATGCCATCCTGCGT-3'. PCR reaction mixture (PCR kit from Eurogentech, Belgium) contained 80 μg of reverse-transcribed cDNA, 1.25±7.5 pM forward primers, 22.5 pM reverse primers and 5 pM probe. For each sample three PCRs were performed. The resulting relative increase in reporter fluorescent dye emission was monitored by the TagMan-system (GeneAmp 5700 sequence detection system and software, Perkin Elmer, Foster City, Calif., USA). The level of the CD95L and CD95 mRNA, relative to β-actin mRNA was calculated using the formula: Relative mRNA expression=$2^{-(Ct\ of\ CD95L - Ct\ of\ b\text{-}actin)}$, where Ct is the threshold cycle value.

Example 13

Transfection and siRNA-mediated knock down. Jurkat T cells and primary human T cells were transfected by lipofection (HiPerfect, Qiagen, Germany) with negative control siRNA oligonucleotides (unlabeled or Alexa 488 labeled non-silencing siRNA, Qiagen, Germany), siRNA oligonucleotides specific for human NDUFAF1: oligo#1 antisense strand: 5'-ACUAACAUCAGGCUUCUCCdTdT-3', oligo#2 antisense strand: 5'-UAACUAUACAUCUGAUUCGdTdT-3' or siRNA oligonucleotides specific for human PKCδ (Hs_P-KKCD_11_HP) and PKCθ (Hs_PRKCQ_5_HP) (Qiagen, Germany). Transfection was performed using $2 \times 10^5$ cells, 9 μl of transfection reagent and different amounts of siRNA oligonucleotides ranging from 75 nM to 900 nM according to manufacturer's instructions. Transfected cells were rested for 48 h before being subjected to further experiments.

Example 14

Measurement of MnSOD activity. MnSOD activity was determined using a commercial kit (Dojindo Molecular Technologies, Japan). $1.5 \times 10^7$ cells were stimulated by plate-bound anti-CD3 antibody (OKT3, 30 μg/ml) or with PMA (10 ng/ml) for different time periods. Cells were harvested and lysed by freezing and thawing. Protein content was adjusted to 1 mg/ml and SOD activity was measured with a photometer according to the manufacturer's instructions. MnSOD activity was assessed after blocking background activity of ZnCuSOD by addition of 1 mM KCN to the reaction mixture.

Example 15

TCR-Induced ROS Generation Depends on the Proximal TCR Signalling Machinery.

Previous studies indicate that TCR stimulation leads to generation of an oxidative signal involving $H_2O_2$ (15, 25). This $H_2O_2$ signal is vital for the initiation of CD95L promoter activity, CD95L expression and AICD (25). In order to identify the components of the transduction cascade mediating ROS generation, we used cells deficient in TCR-signalling molecules. Jurkat cell lines deficient in ZAP70 (68), Lat (19), SLP76 (37) and PLCγ1 (29) were stained with DCFDA and stimulated with plate-bound anti-CD3 antibodies for 30 minutes. All deficient cell lines did not display any oxidative signal, whereas retransfected controls showed a clear increase of ROS upon TCR stimulation (FIG. 1A). Thus, we conclude that TCR-induced generation of ROS depends on ZAP70, Lat and PLCγ1 (FIG. 1C). As PLCγ1 activation results in triggering of PKCs we investigated a possible role of PKCs in oxidative signalling by treating the deficient cell lines with PMA, a PKC activator, which by-passes ZAP70, Lat, SLP76 and PLCγ1. Remarkably, all deficient cell lines revealed a PMA-induced oxidative signal (FIG. 1B). PMA induces an oxidative signal without influencing the intracellular $Ca^{2+}$ level (25). This implicates an involvement of $Ca^{2+}$-independent PKCs in TCR-induced oxidative signalling (FIG. 1C).

Example 16

PKCθ is required for activation-induced generation of ROS.

Figure 2:
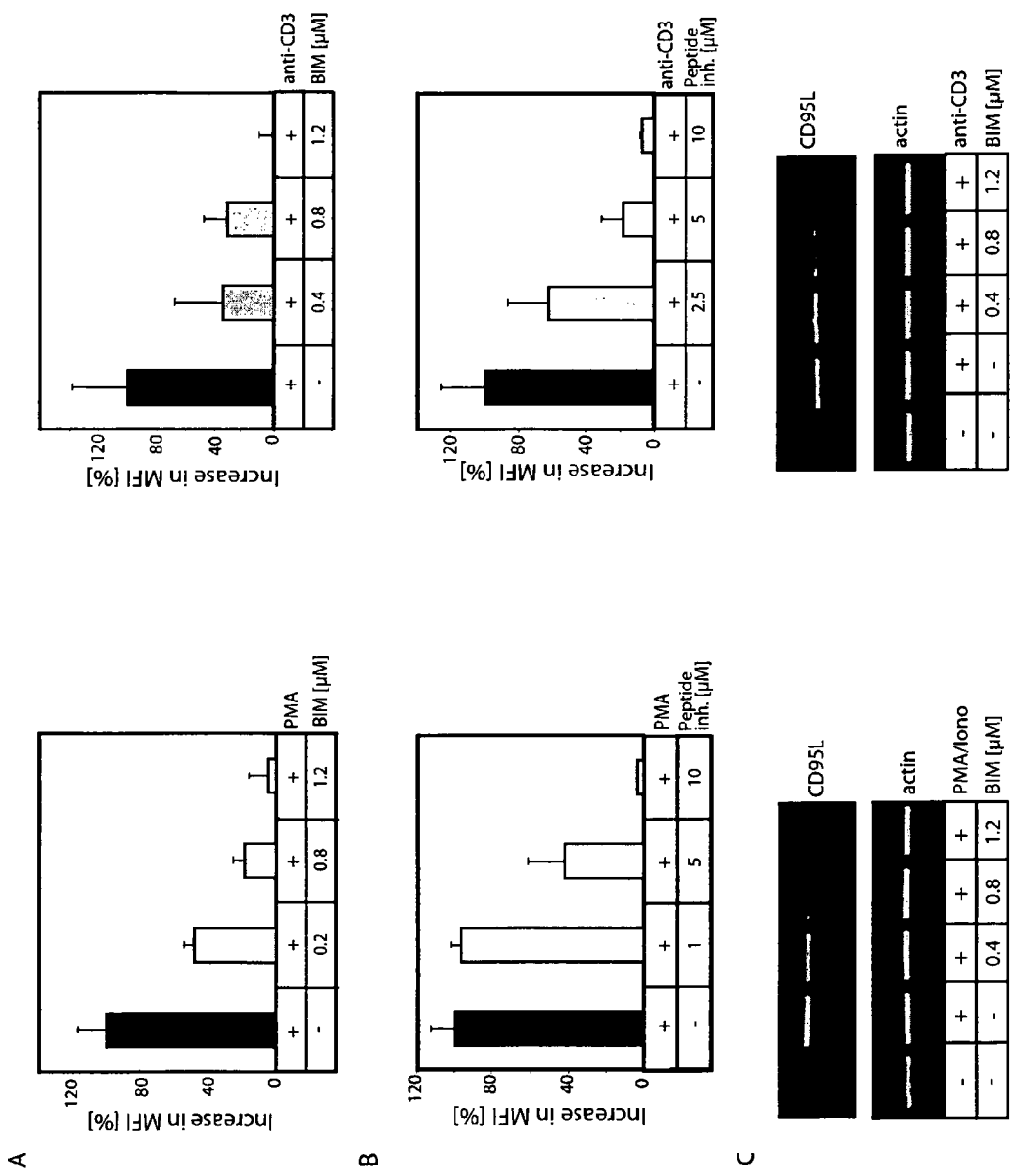
FIG. 2. PKCθ is required for activation-induced generation of ROS. A, J16-145 cells were pretreated with the indicated amounts of the PKC inhibitor BIM and stimulated with PMA (left panel) or via plate-bound anti-CD3 antibodies (right panel) for 30 min. Cells were stained with DCFDA and analysed by FACS. Data shown as percentage of increase in MFI. B, J16-145 cells were pretreated with indicated amounts of general PKC pseudosubstrate peptide inhibitor, stained with DCFDA and stimulated with PMA (left panel) or via plate-bound anti-CD3 antibodies (right panel) for 30 min. ROS levels were measured as in (A). C, J16-145 Jurkat cells were pretreated with the indicated amounts of the PKC inhibitor BIM and stimulated with PMA/ionomycin (left panel) or via plate-bound anti-CD3 antibodies (right panel). After 1 h, RNA was isolated, reverse transcribed, and amplified using CD95L- and actin-specific primers. D, Jurkat J16-145 cells were transfected with 900 nM of scrambled- (ctr) or PKCδ-siRNA oligonucleotides (PKCδ). After 96 h, transfected cells were lysed, and analysed by Western blot for content of PKCδ (right panel) or stained with DCFDA, stimulated via PMA for 30 min, and subjected to FACS analysis (left panel; results are shown as percentage of increase in MFI). E, Jurkat J16-145 cells were transfected with 900 nM of scrambled- (ctr) or PKCδ-siRNA oligonucleotides (PKCθ). 96 h after transfection cells were analysed as described in (D) Western blot for PKCθ content (left panel); PMA-induced DCFDA oxidation (right panel). F, Jurkat J16-145 cells were pretreated with PKCθ pseudosubstrate peptide inhibitor and stimulated with PMA (left panel) or by plate-bound anti-CD3 antibodies (right panel) for 30 min. DCFDA oxidation was measured by FACS and presented as increase of MFI. G, Jurkat cells were transfected with scrambled- (ctr) or PKCθ-siRNA oligonucleotides (PKCθ) (as described in E). Cells were stimulated with PMA/ionomycin. After 1 h, RNA was isolated, reverse transcribed, and amplified using CD95L- and actin-specific primers.
Figure 2:
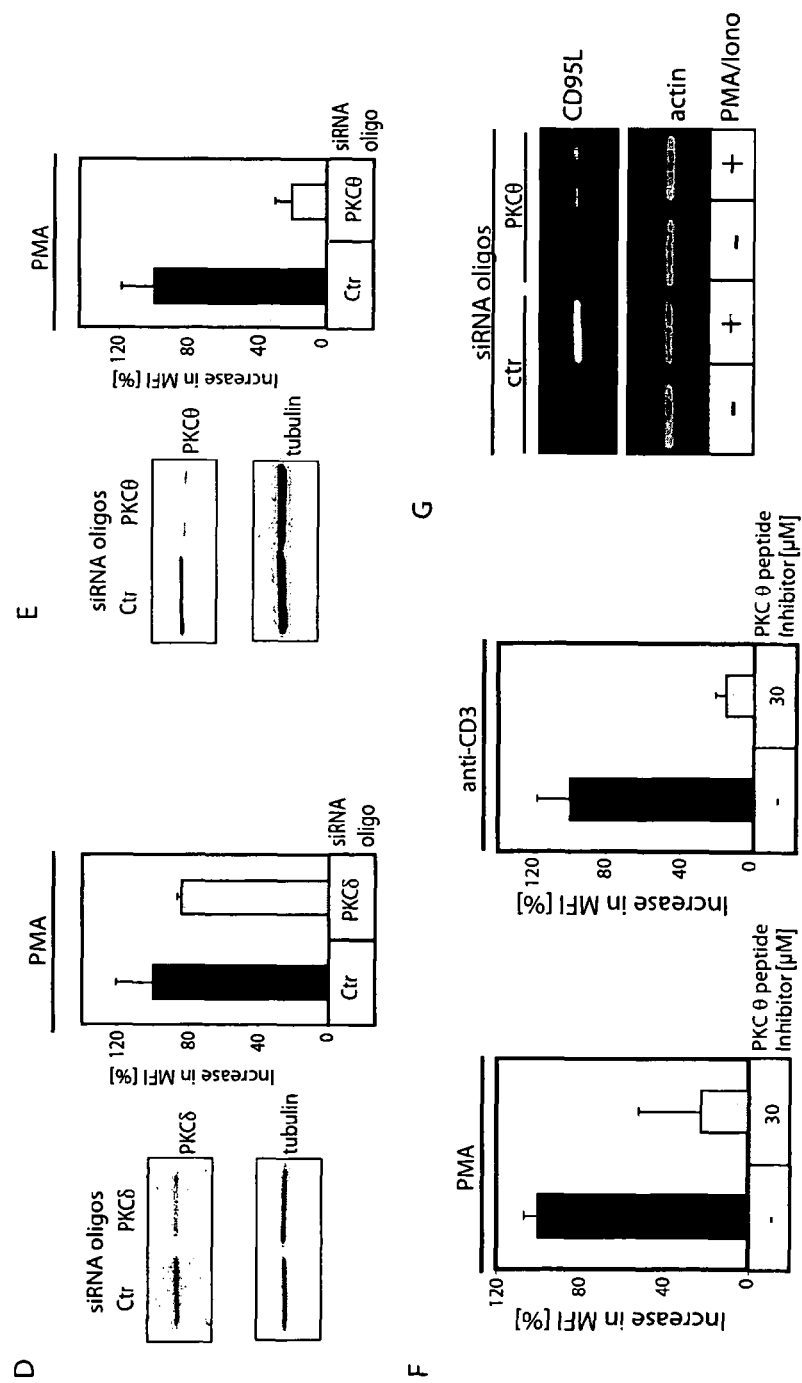

To further corroborate an involvement of PKCs in activation-induced ROS formation cells stimulated via PMA and plate-bound anti-CD3 antibodies were pretreated with the general PKC inhibitor bisindolylmaleimide I (BIM) (FIG. 2A) or a PKC-specific peptide inhibitor (FIG. 2B). Both inhibitors blocked more than 95% of the oxidative signal. Since ROS cooperates with $Ca^{2+}$ signalling for CD95L induction (25) we analysed the impact of BIM on CD95L expression. Cells stimulated via anti-CD3 antibodies and PMA/ionomycin were pretreated with BIM. RNA was isolated, reverse-transcribed, and amplified using CD95L specific primers. In BIM treated cells a dose dependent inhibition of CD95L expression was detectable (FIG. 2C). Considering that activation-induced oxidative signalling is inducible by PMA alone (FIG. 1B), we focused on $Ca^{2+}$-independent novel PKC isoforms (nPKC). It has been reported that PKCδ, a nPKC isoform, is involved in ROS generation in keratinocytes upon overexpression (39) and in PMA/ionomycin treated myeloid leukemia cells (43). However, despite down-modulating PKCδ via siRNA, the oxidative signal was not significantly affected (<20% decrease) (FIG. 2D). This implies that PKCδ only plays a minor role in generation of activation-induced ROS. PKCθ is unique among the nPKC isoforms because it is indispensable for T cell development and activation (48, 59, 64). To analyze the impact of PKCθ on activation-induced ROS production, cells were transfected with PKCθ siRNA oligonucleotides (FIG. 2E). More than 80% of the PMA-induced oxidative signal was inhibited in cells transfected with PKCθ siRNA oligonucleotides as compared to the control. These data were further confirmed by treating Jurkat cells with a PKCθ-specific peptide inhibitor, which significantly reduced the TCR- and the PMA-induced ROS levels (FIG. 2F). Moreover, siRNA mediated down-modulation of PKCθ results in an inhibition of CD95L expression (FIG. 2G). Thus, we conclude that PKCθ is crucial for activation-induced ROS formation and CD95L expression.

Example 17

Activation-Induced ROS Generation is Partially NADPH Oxidase Dependent.

Recently, it has been shown in NOX2 deficient mice that TCR-induced ROS generation is, at least partially, dependent on NOX2 (30). Here we analysed a potential role of NADPH oxidases in human T cells. Jurkat cells were preincubated with DPI, a rather unspecific but commonly used NADPH oxidase inhibitor (14, 42, 55, 57, 61) or the specific NADPH oxidase inhibitor apocynin (60) and thereafter treated with PMA as an NADPH oxidase activator. Application of both, DPI and apocynin showed only a moderate effect on PMA-induced ROS generation in Jurkat cells (FIG. 3A, B). To control whether the applied amounts of inhibitors are sufficient to block NADPH oxidase, neutrophils were treated with PMA (10 ng/ml) and cotreated with DPI and apocynin. PMA induces a massive NADPH oxidase dependent ROS release in neutrophils called "oxidative burst". The "oxidative burst" could be inhibited almost completely (up to 91% inhibition) by application of 100 µM DPI or 600 µM apocynin. The same amounts of inhibitors block in Jurkat cells less than 60% of the PMA-induced oxidative signal (FIG. 3A, B). Since downmodulation of PKCθ expression inhibited more than 80% of the oxidative signal (FIG. 2E), the existence of an additional PKCθ-dependent source of ROS in human T cells has to be postulated.

Example 18

Cells Depleted in Mitochondrial DNA Show an Impaired Activation-Induced ROS Generation and AICD.

Besides NOX2, mitochondria are a prominent source of ROS. It has been reported that upon PMA treatment PKCδ can be translocated into/to mitochondria (39, 43). To determine whether PKCθ is translocated to mitochondria Jurkat cells were stimulated with PMA. PKC translocation was assessed by subjecting cytoplasmic, mitochondrial and plasma membrane fractions to immunoblotting with anti-PKC antibodies. Surprisingly, PKCδ and PKCθ were detected in the plasma membrane fraction already in unstimulated cells. However, as expected, PKCδ translocates to the mitochondria after stimulation. Interestingly, the amount of PKCθ increases also in the mitochondrial fraction upon PMA treatment (FIG. 4A). Thus, PKCθ and PKCδ are translocated to the mitochondria and/or associated membranes in T cells after activation (FIG. 4B). In order to analyse the role of mitochondria in activation-induced ROS generation in more detail, cells transiently depleted in mtDNA, pseudo-$\rho^0$ cells, were generated by short exposure (6-21 days) to low amounts of ethidium bromide (FIG. 4C) (12, 36). Upon stimulation with anti-CD3 or PMA, pseudo-$\rho^0$ cells exhibited an up to 60% diminished oxidative signal (FIG. 4D). Since the activation-induced oxidative signal is crucial for AICD pseudo-$\rho^0$ cells displayed a massive reduction of AICD upon TCR-stimulation and PMA/ionomycin treatment (FIG. 4E). The depletion of mtDNA was entirely reversible after removal of ethidium bromide from cell culture for 21-23 days (FIG. 4F). In concordance with recovery of mitochondrial protein expression, activation-induced ROS generation (FIG. 4G) and AICD (FIG. 4H) regained its normal level. Thus, we demonstrate here that mitochondrial function is a prerequisite for induction of AICD.

Example 19

Complex I of the Mitochondrial ETC is the Source of Activation-Induced ROS Formation.

Figure 3:
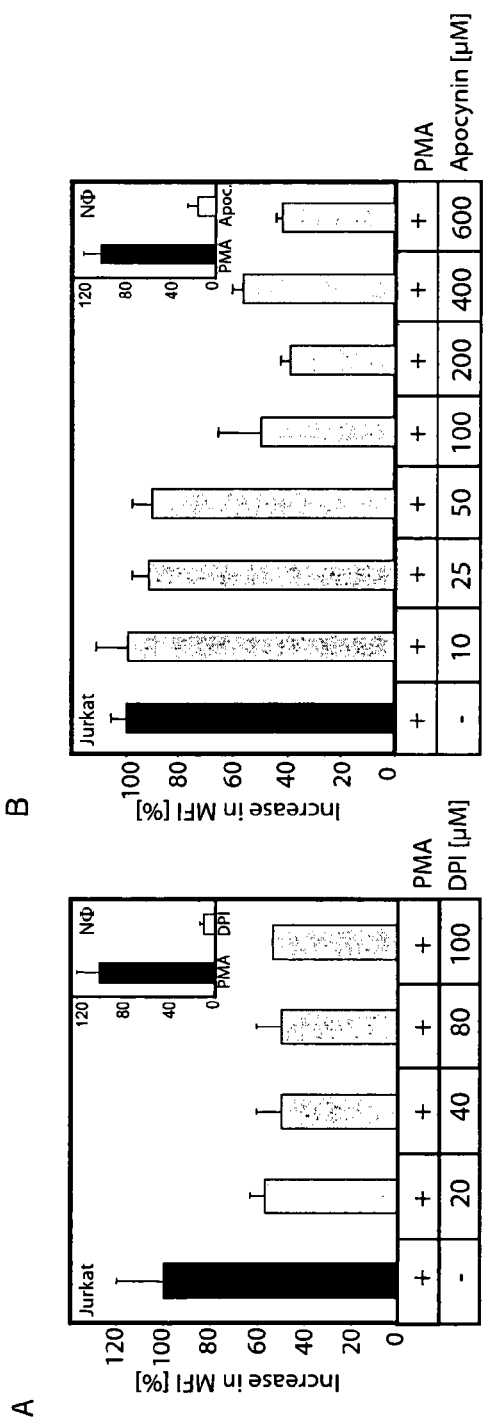
FIG. 3. Activation-induced ROS generation is partially NADPH oxidase dependent. A, B, Jurkat J16-145 cells were pretreated with NADPH oxidase inhibitors DPI (A) and apocynin (B), stained with DCFDA and stimulated with PMA for 30 min. Inserts show neutrophils (NO) stimulated with PMA (10 ng/ml) and cotreated with DPI (100 μM) (A) or apocynin (600 μM) (B) to inhibit the NADPH oxidase dependent "oxidative burst". Data are presented as FACS-measured increase of MFI of oxidised DCFDA.
Figure 5:
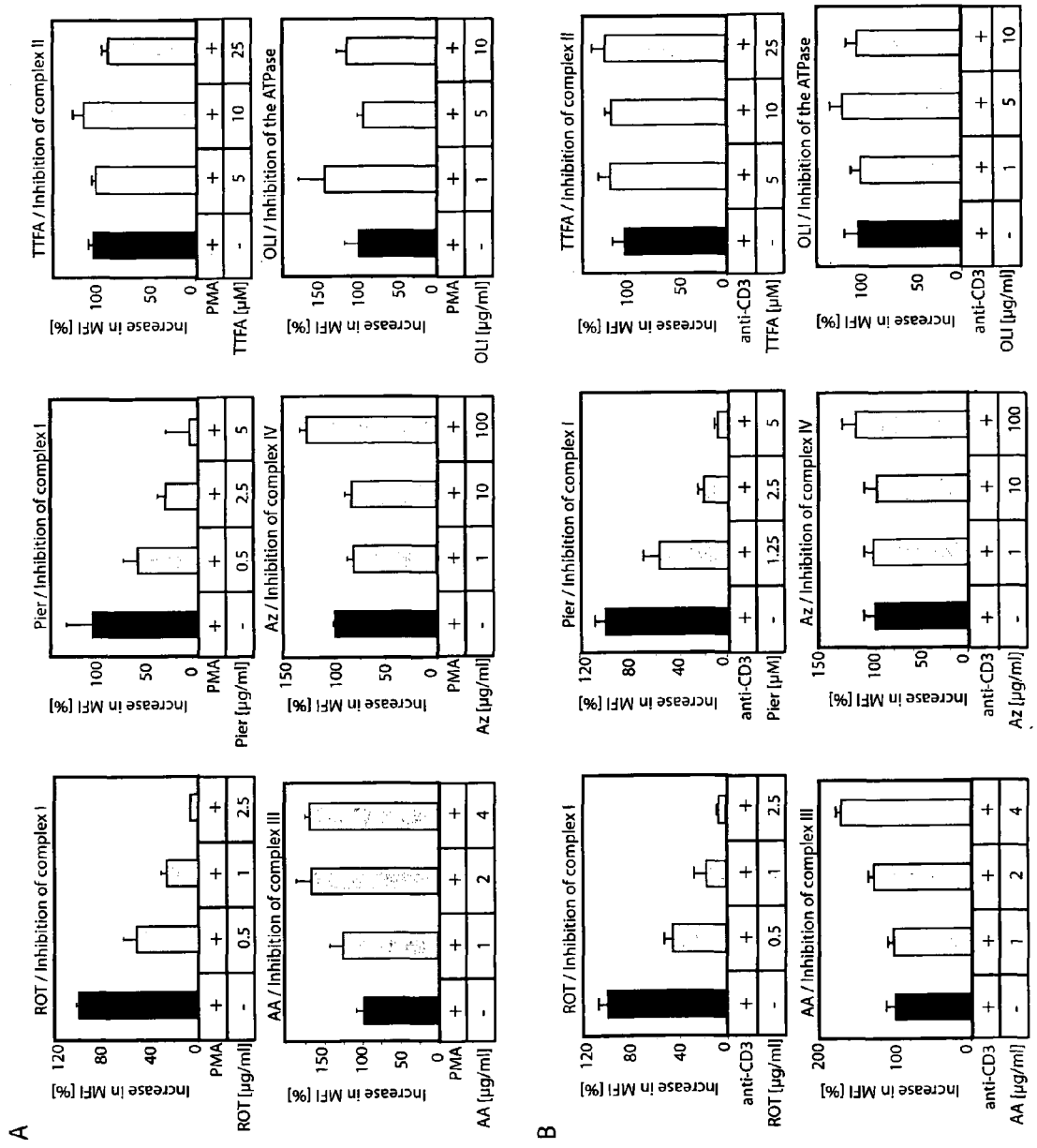
FIG. 5. Complex I of the mitochondrial ETC is the source of activation-induced ROS formation A, B, Jurkat J16-145 cells were pretreated with the indicated amounts of ETC inhibitors (ROT—rotenone; Pier—piericidin A; AA—antimycin A; Az—sodium azide) or an inhibitor of the F0F1-ATPase (OLI—oligomycin), stained with DCFDA and stimulated by PMA (A) or via plate-bound anti-CD3 antibody (B) for 30 min and analysed by FACS. The data are presented as percentage of increase in MFI. C, Jurkat J16-145 cells were treated with high concentrations of inhibitors of the ETC or the F0F1-ATPase for 2 h. Thereafter, cells were lysed and ATP content was determined. D, Mitochondria-derived ROS induce changes in expression and activity of MnSOD. Jurkat J16-145 cells were stimulated with plate bound anti-CD3 antibodies or PMA/ionomycin (Iono) for the indicated time period. Isolated RNA was reverse-transcribed, and amplified using MnSOD-specific primers. E, Jurkat cells were stimulated via plate bound anti-CD3 antibodies or PMA/ionomycin (Iono) for the indicated time points. Cells were lysed and MnSOD protein levels were determined by Western blot analysis. MnSOD expression was normalized to tubulin and quantified using NIH Image (lower panel). F, MnSOD activity in mitochondria of J16-145 cells stimulated by plate-bound anti-CD3 antibody or PMA.
Figure 5:
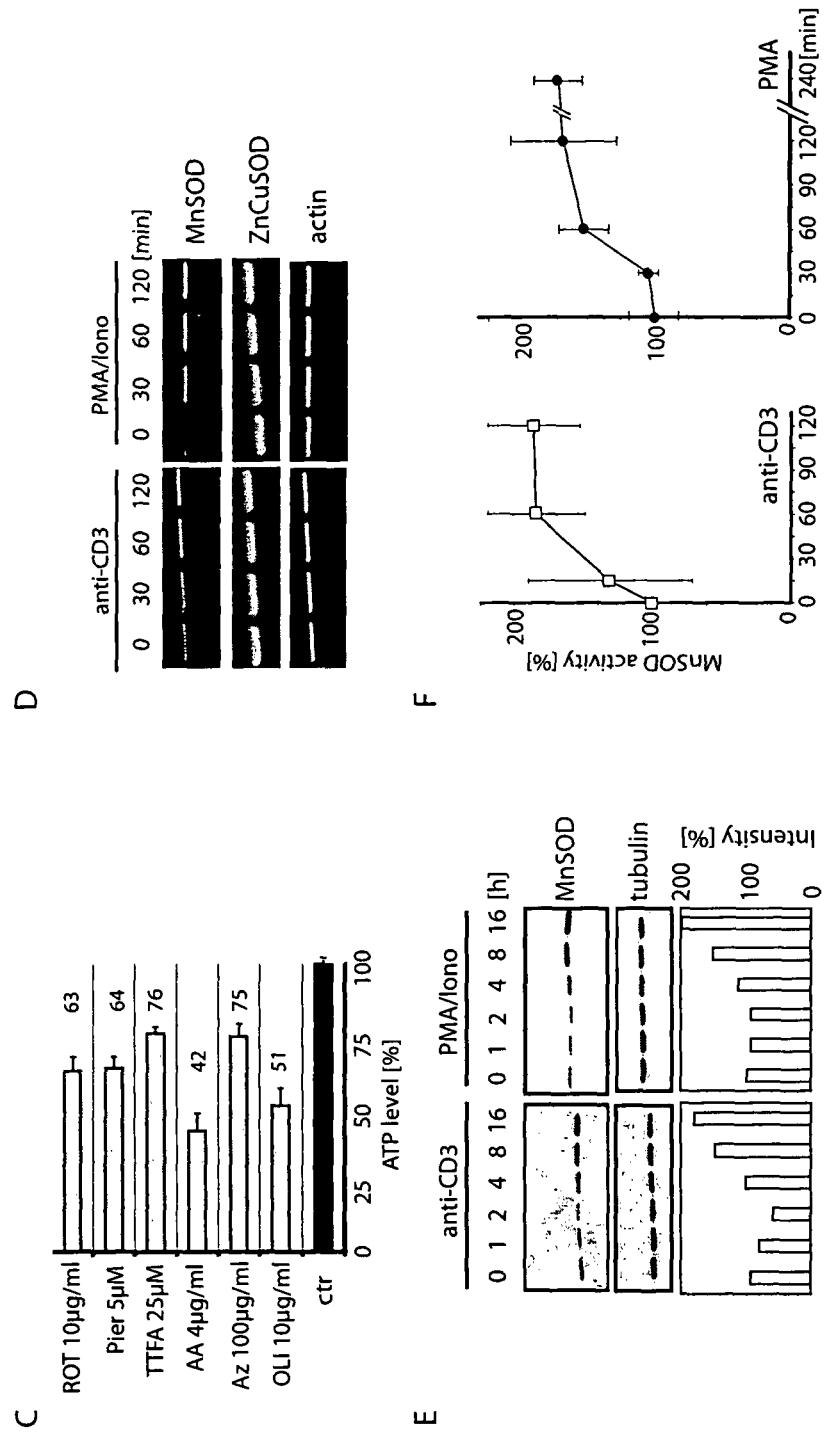

Since depletion of mtDNA leads to a decrease in activation-induced ROS generation, mtDNA-encoded proteins have to be involved in oxidative signalling. Most enzymes of the ETC are oligomeric complexes consisting of both nuclear DNA- and mtDNA-encoded subunits. The primary sites for mitochondrial ROS production are the complexes I and III of the ETC (45). Therefore, we aimed at analysing the role of these complexes in activation-induced ROS production. Complex I was blocked by rotenone, a commonly used inhibitor. However, rotenone is also known to interfere with a couple of cellular pathways including tubulin-depended signalling events (8, 16, 32, 52). Thus, we also used a second more specific inhibitor, namely piericidin A (13, 28). Complex II was inhibited by application of 1,1,1-thenoyl trifluoroacetone (TTFA), complex III by antimycin A, complex IV by sodium azide and the $F_0F_1$ ATPase was blocked by oligomycin. Cells were pretreated with these inhibitors and subsequently stimulated with anti-CD3 antibodies or PMA. Thereafter, generation of ROS was determined. Only rotenone and piericidin A were able to inhibit activation-induced ROS generation, whereas TTFA, antimycin A, sodium azide, and oligomycin had no effect or increased the oxidative signal (FIG. 5A, B). ATP levels could not account for inhibition of ROS generation, since oligomycin and antimycin A treatment resulted in a more efficient ATP depletion as compared to rotenone and piericidin A (FIG. 5C). In contrast to inhibition of the NADPH oxidase (max. 60% blockage of ROS generation; FIG. 3), inhibition of complex I leads to a blockage of more than 95% of activation-induced ROS production (FIG. 5A, B). Therefore, complex I is not only the source of mitochondria-derived ROS but also its activity seems to be a prerequisite for subsequent ROS production via the NADPH oxidase.

Example 20

Activation-Induced ROS Enhances Expression and Activity of Mitochondrial MnSOD.

It has been demonstrated that complex I releases superoxide anion ($O_2^-$) into the mitochondrial matrix (65). However, it is cytosolic $H_2O_2$ which plays a crucial role in CD95L expression (25). Since $O_2^-$ cannot cross membranes (53) and leave the mitochondria it has to be converted to membrane permeable $H_2O_2$ by MnSOD to act as a second messenger in induction of AICD. To analyse whether TCR stimulation and PMA treatment results in an upregulation of MnSOD transcription, Jurkat cells were stimulated with plate-bound anti-CD3 antibodies or treated with PMA/ionomycin. RNA was isolated and reverse-transcribed. After 60 min a moderate increase in the transcript level of MnSOD was detected in CD3-stimulated and PMA/ionomycin-treated cells, whereas cytosolic ZnCuSOD level remained unchanged (FIG. 5D). In addition, induction of MnSOD on protein level was analysed. Cells were stimulated with anti-CD3 antibodies or PMA/ionomycin and lysed at the indicated time points. After 4 hours of stimulation an increase in MnSOD protein level was observed (FIG. 5E). To verify these data, activity of MnSOD was determined. PMA treatment and CD3 stimulation led to a fast increase of MnSOD activity (FIG. 5F). Thus, complex I derived ROS is transformed to $H_2O_2$ and therefore, it can serve as a second messenger in regulation of CD95L expression (25) (FIG. 6D).

Example 21

Complex I Derived ROS are Crucial for Induction of CD95L Expression.

Figure 6:
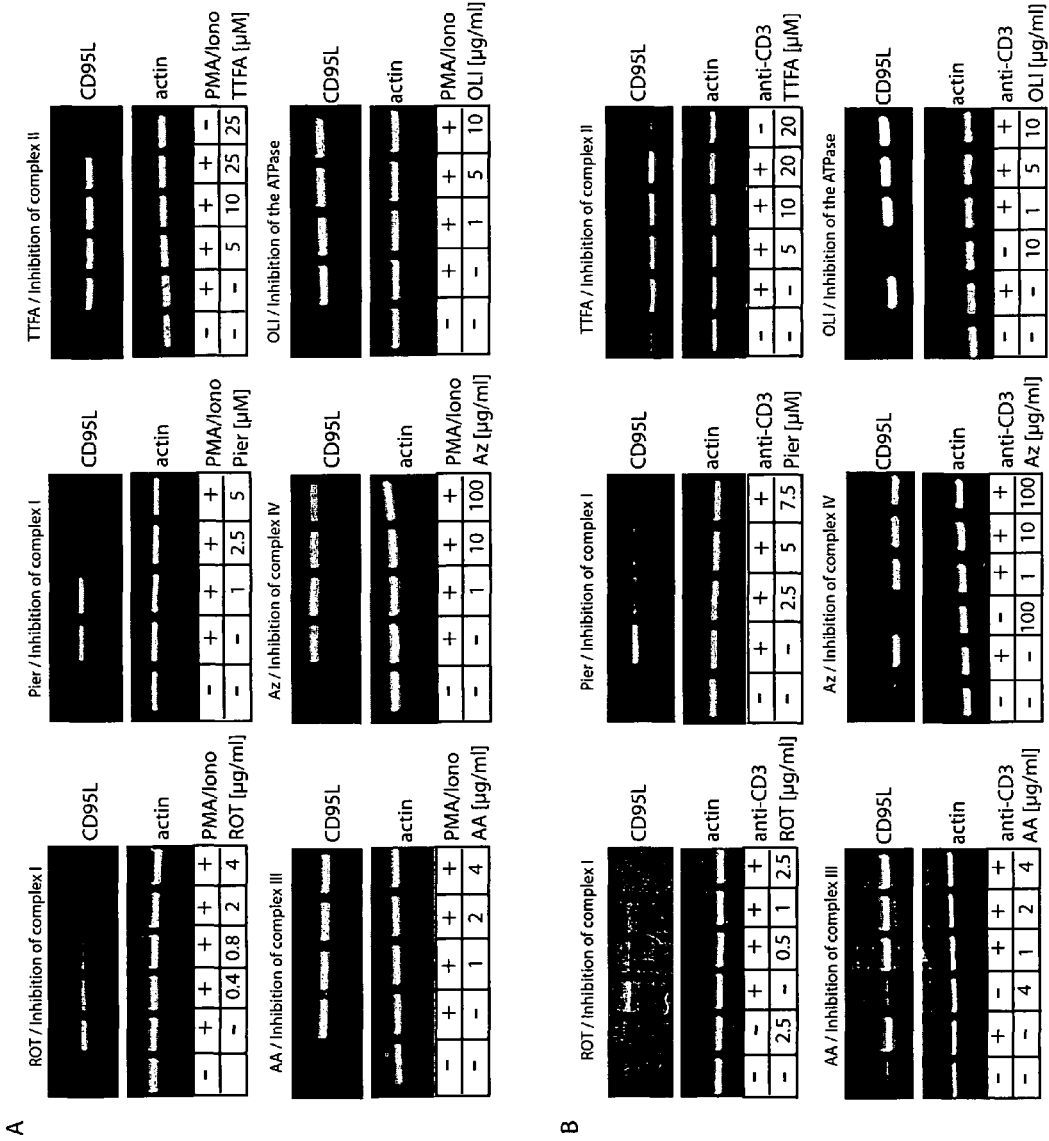
FIG. 6. ROS produced by complex I drive activation-induced CD95L expression A, B, J16-145 cells were pretreated with the indicated amounts of inhibitors of the ETC (ROT—rotenone; Pier—piericidin A; AA—antimycin A; Az—sodium azide) or the F0F1-ATPase (OLI—oligomycin) and stimulated with PMA/ionomycin (Iono) (A) or plate-bound anti-CD3 antibodies (B) for 1 h. RNA was isolated, reverse-transcribed, and amplified using CD95L- and actin-specific primers. C, J16-145 cells were pretreated with the indicated inhibitors and stimulated with (left panel) or without (right panel) plate-bound anti-CD3 antibodies for 1 h. RNA was isolated, reverse-transcribed, and a quantitative PCR was performed. CD3 induced CD95L expression was set to 100%. All other values were calculated according to the CD3 induced CD95L expression. D, Schematic diagram of mitochondrial ROS production. $C_I$=complex I.
Figure 6:
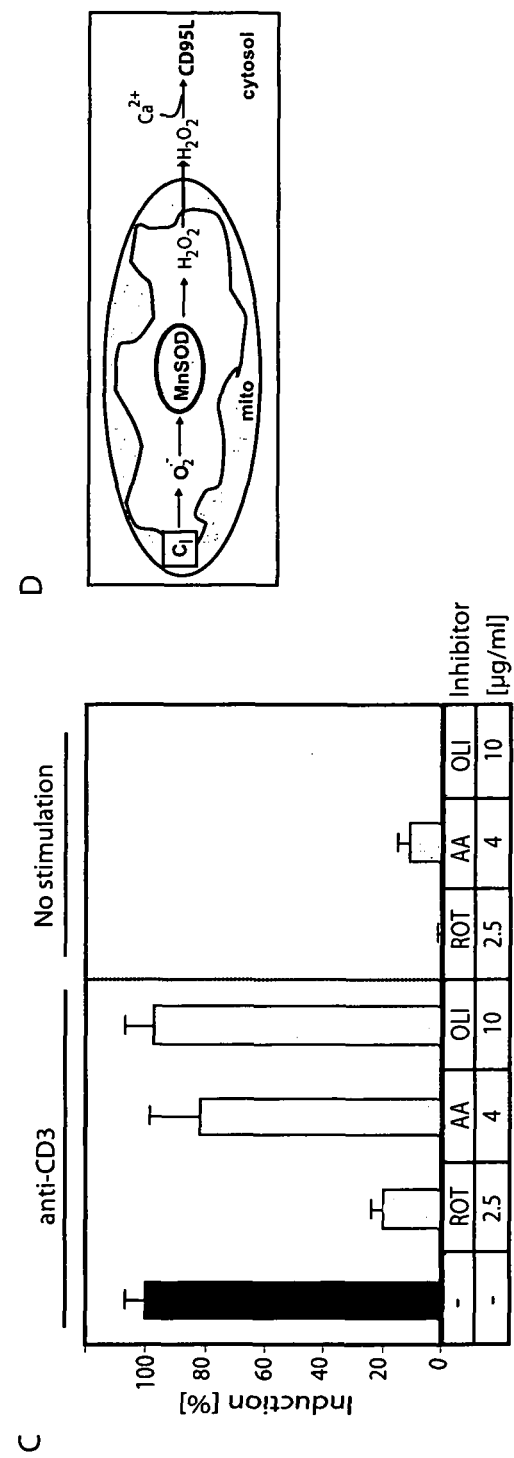

To analyse the role of complex I derived ROS in activation-induced CD95L expression we inhibited all components of the ETC. Cells were stimulated by CD3 triggering (FIG. 6A)

or PMA/ionomycin treatment (FIG. 6B) in the presence or absence of inhibitors. After 1 hour of treatment RNA was isolated, reverse-transcribed and amplified using CD95L-specific primers. Significant levels of CD95L transcripts were not detected in unstimulated cells, whereas CD3 triggering and PMA/ionomycin (FIG. 6A, B) stimulation resulted in a strong expression of CD95L. The complex I inhibitors, rotenone and piericidin A, abolished CD95L transcription almost completely, whereas blocking the other complexes of the ETC had no effect (FIG. 6A, B). To verify these data a quantitative PCR was performed. Stimulation of Jurkat cells with anti-CD3 antibodies displayed a strong induction of CD95L expression. Rotenone treatment resulted in a more than 80% reduction of CD95L induction, whereas antimycin A and oligomycin showed no effect (FIG. 6 C). Upon 2 h of treatment, applied doses of all inhibitors were in a sub-toxic range (FIG. 8A), thus their toxicity can not account for inhibition of activation-induced ROS production and CD95L expression. Therefore, ROS generated from complex I are a prerequisite for induction of CD95L expression (FIG. 6D).

Example 22 siRNA-Mediated Downregulation of NDUFAF1 Expression Inhibits Activation-Induced ROS Signalling, CD95L Expression and AICD.

Figure 7:
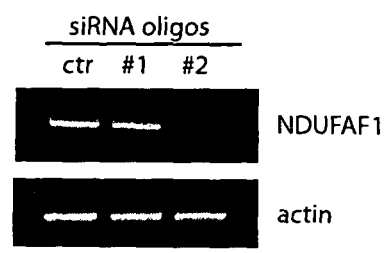
FIG. 7. Downregulation of NDUFAF1 inhibits ROS generation, CD95L expression and AICD. A, J16-145 cells were transfected with 75 nM scrambled- (ctr) or two different NDUFAF1-siRNA oligonucleotides (#1, #2). After 48 h RNA was isolated, reverse-transcribed, and amplified using NDUFAF1- and actin-specific primers. B, 48 h after transfection with scrambled- (ctr) or NDUFAF1-siRNA oligonucleotides (#1, #2) the oxidative signal upon 30 min of PMA treatment was determined by DCFDA staining (filled profile—stained cells/untreated; open profile—cells stained and stimulated with PMA). C, Quantification of PMA-induced oxidative signals in Jurkat cells. 72 h after transfection with 75 nM scrambled- (ctr) or NDUFAF1-siRNA oligonucleotides (#1, #2). Cells were stained with DCFDA, treated with PMA for 30 min and subjected to FACS analysis. Results are shown as percentage of increase in MFI. D, J16-145 cells were transfected with 75 nM of scrambled- (ctr) or NDUFAF1-siRNA oligonucleotides (#1, #2). After 72 h of resting, cells were treated with PMA/ionomycin for 1 h. PMA/ionomycin RNA was isolated, reverse-transcribed, and amplified using CD95L-, and actin-specific primers. E, J16-145 cells were transfected with 75 nM (left panel) or 900 nM (right panel) of scrambled- (ctr) or NDUFAF1-siRNA #2 oligonucleotides. After 72 h of resting AICD was induced by 24 h of PMA/ionomycin treatment. Cell death was assessed by a drop in FSC/SSC index. Results were recalculated to "specific cell death".
Figure 7:
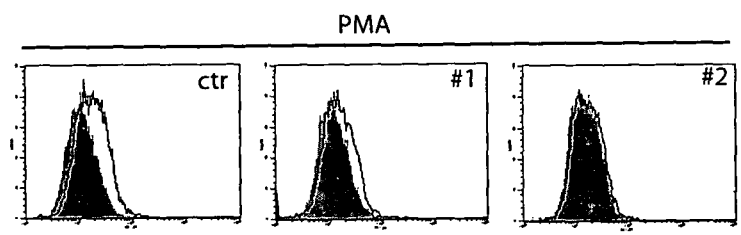
Figure 7:
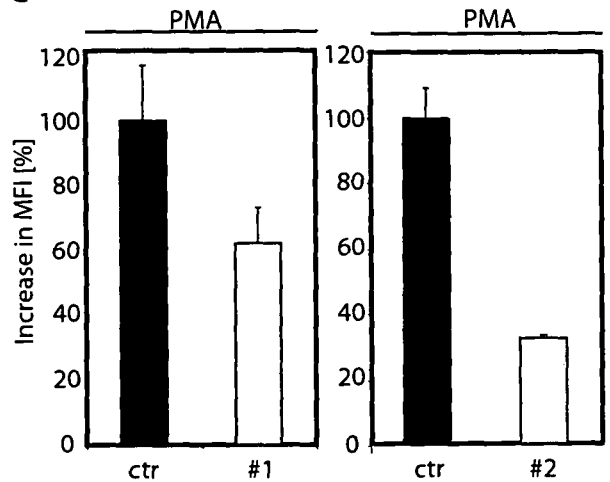
Figure 7:
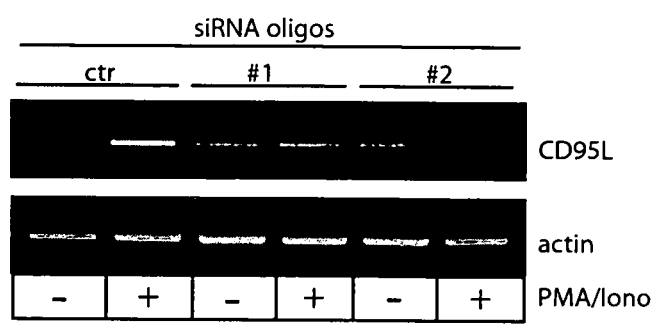
Figure 7:
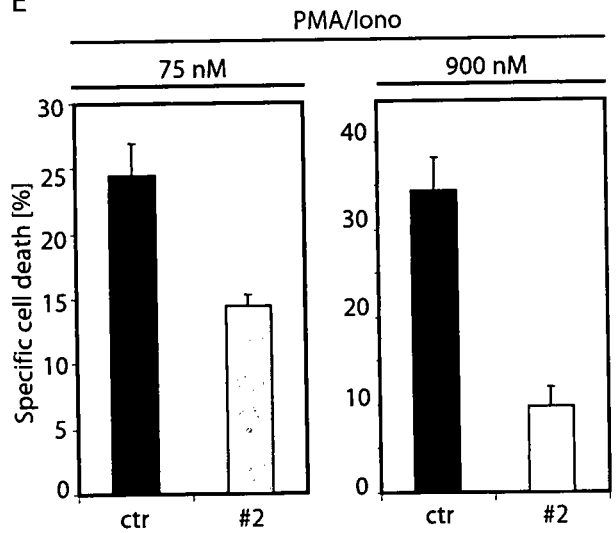

In addition to pharmacological manipulation of mitochondrial respiration, we sought for other ways to abolish complex I function and inhibit activation-induced ROS signalling. Mammalian complex I consists of at least 46 subunits (10). 39 of them are encoded by nuclear DNA and may be a potential target for siRNA-mediated downregulation. Recently, it has been shown that NDUFAF1, a human homologue of CIA30—a complex I chaperone of *Neurospora crassa*—is essential for assembly of complex I in humans (31, 66). Reducing the amount of NDUFAF1 by siRNA led to a lowered abundance and activity of complex I (66). To knock down NDUFAF1 expression, we used two different siRNA oligonucleotides (66). Both siRNAs displayed a knock down effect with siRNA oligonucleotide #2 mediating a stronger inhibition of NDUFAF1 expression (FIG. 7A). Remarkably, both oligonucleotides diminished the oxidative signal induced by PMA (oligonucleotide #1 up to 39% and oligonucleotide #2 up to 68%) (FIG. 7B, C). Since the oxidative signal generated by complex I is required for CD95L expression (FIG. 6A, B), downregulation of the NDUFAF1 level has to influence transcription of CD95L. Jurkat cells transfected with NDUFAF1 siRNA oligonucleotides were stimulated with PMA/ionomycin. After 1 h of treatment RNA was isolated, reverse-transcribed and amplified using CD95L-specific primers. Cells transfected with control oligonucleotides showed a normal expression of CD95L, whereas cells transfected with NDUFAF1 siRNA displayed a strongly diminished CD95L expression (FIG. 7D). In addition, the role of complex I in AICD was analysed in cells transfected with NDUFAF1 siRNA oligonucleotides. AICD was determined after 24 h of PMA/ionomycin treatment. In comparison to control cells, cells transfected with NDUFAF1 siRNA oligonucleotides displayed a significant inhibition of cell death (FIG. 7E). Thus, we prove that complex I assembly and ROS formation are crucial for AICD induction.

Example 23

Metformin Inhibits Complex I Derived ROS, Activation-Induced CD95L Expression, and AICD.

Figure 8:
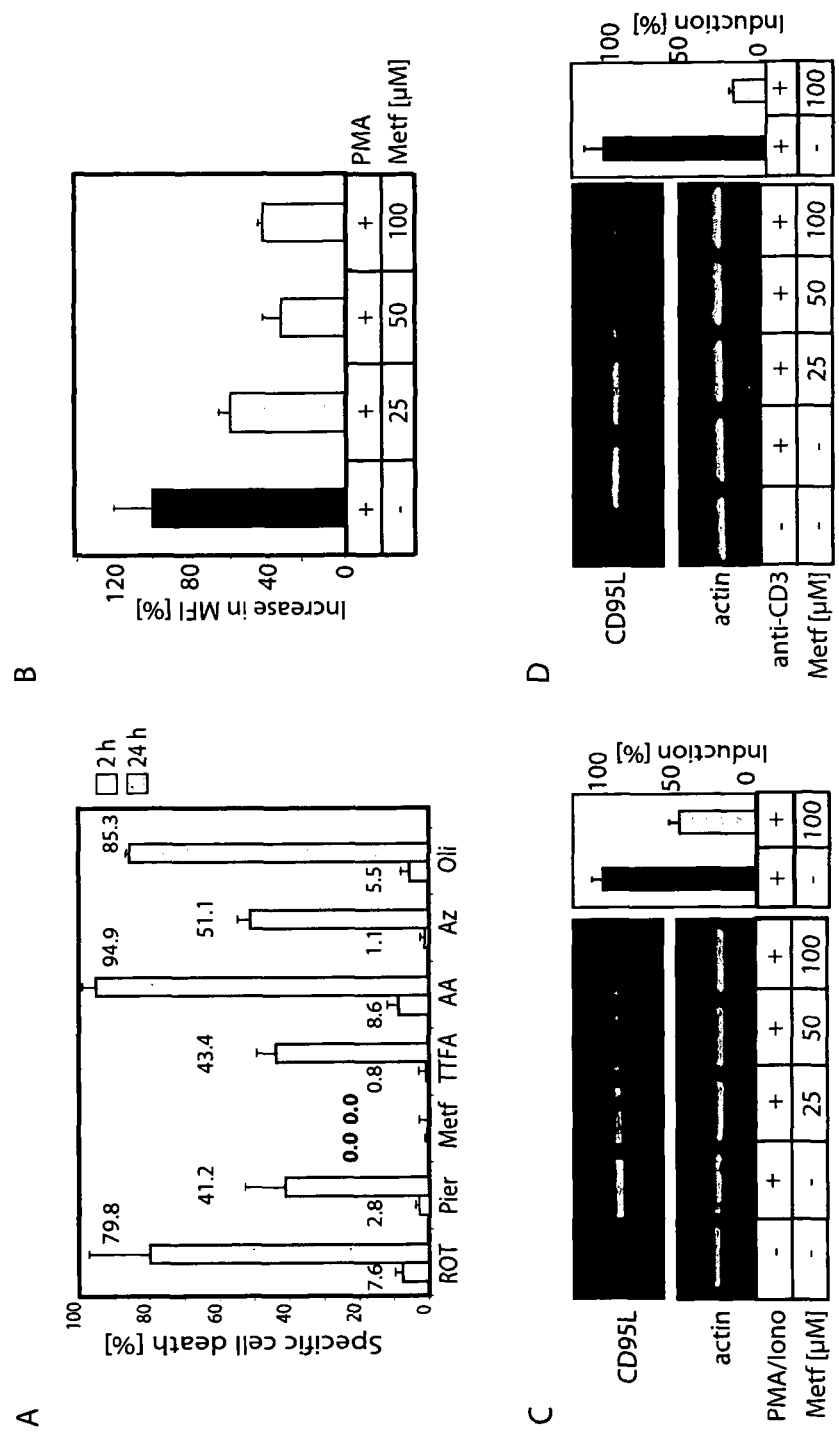
FIG. 8. Metformin, a non-toxic complex I inhibitor, blocks activation-induced oxidative signal, CD95L expression and AICD. A, Metformin induces no toxicity. J16-145 cells were treated for 2 h (white bars) and 24 h (grey bars) with the indicated inhibitors. Cell death was determined by a drop in forward-to-side-scatter profile in comparison to living cells and recalculate to "specific cell death". (ROT—rotenone [10 µg/ml]; Pier—piericidin A [7.5 µM]; Metf—metformin [100 µM]; TTFA—1,1,1-thenoyl trifluoroacetone [25 µM]; AA—antimycin A [4 µg/ml]; Az—sodium azide [100 µg/ml]; OLI—oligomycin[10 µg/ml]). B, J16-145 cells were pretreated with indicated amounts of metformin, stained with DCFDA and stimulated by PMA for 30 min. Oxidative signal was quantified as increase in MFI. C, D, J16-145 cells were pretreated with the indicated amounts of metformin and stimulated with PMA/ionomycin (Iono) (C) or plate-bound anti-CD3 antibodies (D) for 1 h. Next, RNA was isolated, reverse-transcribed, and amplified using CD95L- and actin-specific primers (left panel). In addition, a quantitative PCR was performed (right panel). CD3 induced CD95L expression was set to 100%. All other values were calculated according to the CD3 induced CD95L expression. E, F, J16-145 cells pretreated with the indicated amounts of metformin and AICD was induced by PMA/ionomycin (Iono) treatment (E) or stimulation with plate-bound anti-CD3 antibodies (F). After 24 h cell death was assessed by drop in FSC/SSC index. Inserts (E, F) show J16-145 cells cotreated with or without CD95L neutralizing antibody and stimulated by plate-bound anti-CD3 antibodies. Results were recalculated to "specific cell death".
Figure 8:
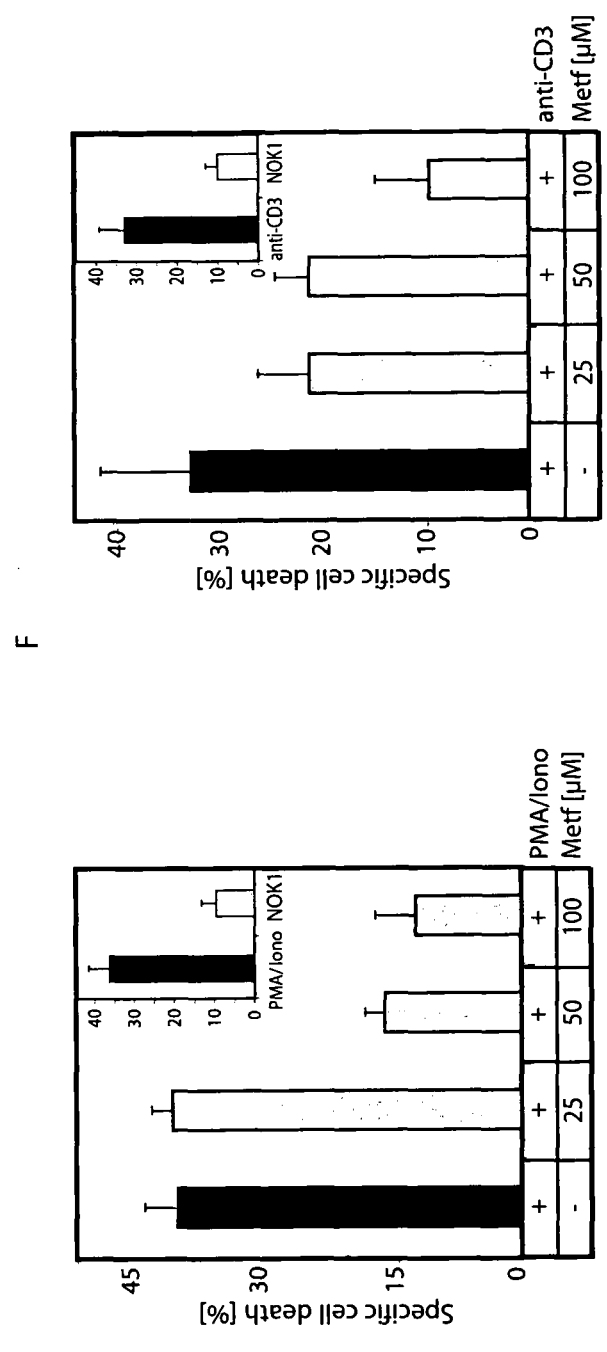

In search for potential tools to manipulate ROS generation at complex I and treat CD95/CD95L-dependent disorders, we applied metformin, a drug widely used in treatment of type II diabetes (2, 3, 58). Metformin has recently received attention due to its effects on mitochondria (6, 18, 23). It has been demonstrated, that metformin mildly inhibits complex I (6, 18). In addition, metformin can efficiently inhibit complex I-induced ROS production in isolated mitochondria, an effect that was linked to blockage of reversed electron flux (6). Since metformin showed no toxicity on Jurkat cells (FIG. 8A) it is an ideal tool to investigate the impact of complex I-mediated ROS production on AICD. Jurkat cells pretreated with metformin and stained with DCFDA exhibited a diminished oxidative signal after treatment with PMA (FIG. 8B). Concordantly, they also displayed an inhibition of CD95L expression upon PMA/ionomycin treatment and TCR triggering (FIG. 8C, D). A quantitative PCR revealed that cells stimulated with PMA/ionomycin and cotreated with metformin displayed a 50% reduction of CD95L expression (FIG. 8C). Even more remarkably, upon TCR triggering metformin inhibits CD95L expression up to 80% (FIG. 8D). AICD in Jurkat cells is mainly CD95L dependent (FIG. 8E, F). To study the effect of metformin on AICD, Jurkat cells were either stimulated with PMA/ionomycin (FIG. 8E) or plate-bound anti-CD3 antibodies (FIG. 8F). Cells pretreated with metformin showed a drastically reduced AICD. Apoptosis induced via direct stimulation of the CD95 receptor was not affected by metformin (data not shown). Thus, blockage of AICD by metformin is due to inhibition of CD95L expression.

Example 24

Inhibition of Complex I Blocks AICD in Primary Human T Cells.

Figure 9:
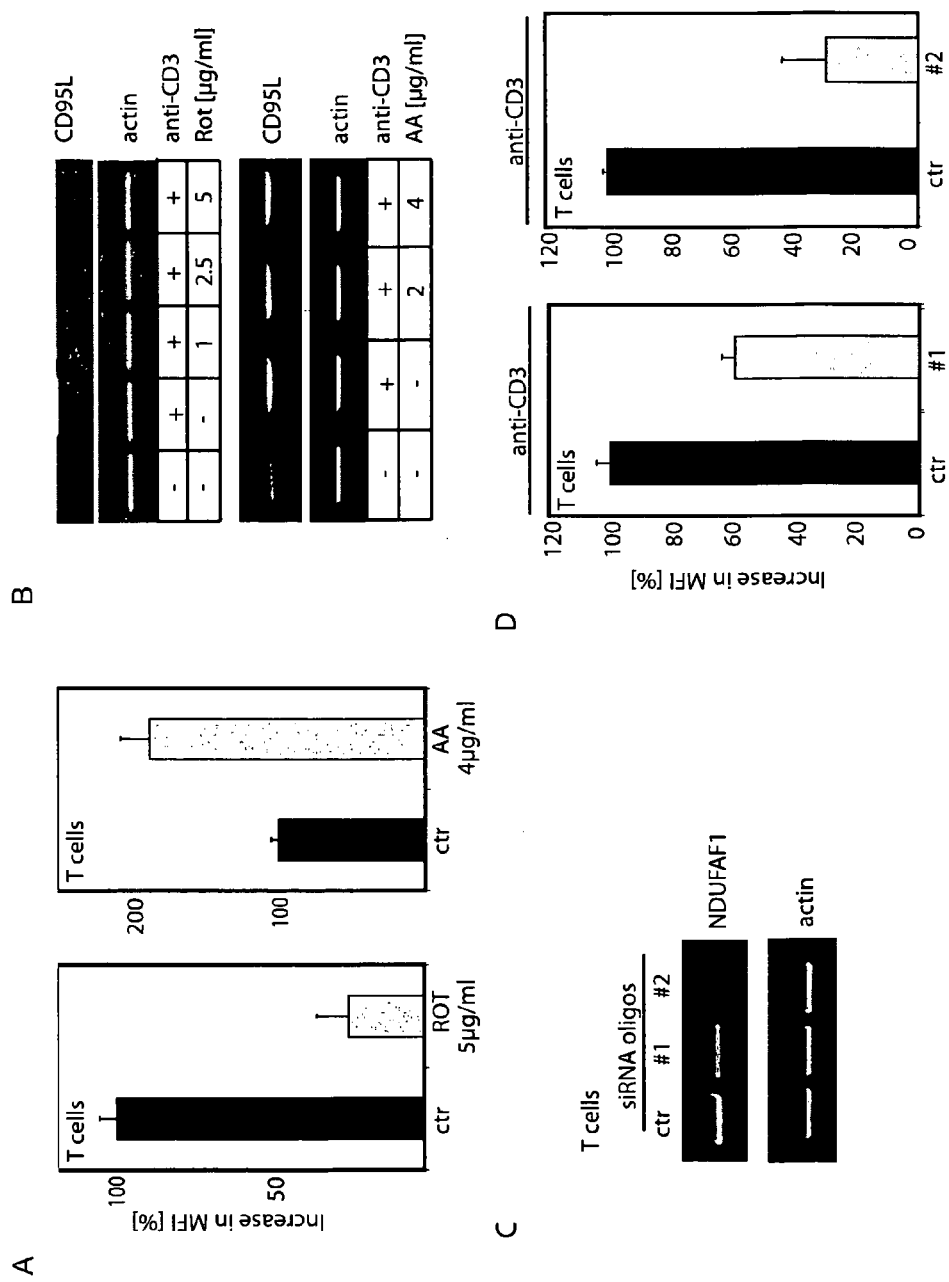
FIG. 9. Primary human T cells depend on complex I-originated activation-induced ROS for CD95L expression and AICD. A, T cells were pretreated with the indicated amounts of inhibitors of the ETC (ROT—rotenone and AA—antimycin A) and stimulated with anti-CD3 antibodies for 30 min. Cells were stained with DCFDA and MFI was measured by FACS. B, T cells were pretreated with indicated amounts of rotenone (upper panel) or antimycin A (lower panel) and stimulated with anti-CD3 antibodies for 1 h. Next, RNA was isolated, reverse-transcribed, and amplified using CD95L- and actin-specific primers. C, T cells were transfected with 900 nM of scrambled- (ctr) or two different NDUFAF1-siRNA oligonucleotides (#1, #2). After 48 h, RNA was isolated, reverse-transcribed, and amplified using NDUFAF1- and actin-specific primers. D, 72 h after transfection with 900 nM of scrambled- (ctr) or NDUFAF1-siRNA oligonucleotides (#1, #2) primary human T were stimulated by plate-bound anti-CD3 antibodies for 30 min and oxidative signal was determined as in (A). E, F, G, The T cells were pretreated with indicated amounts the non-toxic complex I inhibitor, metformin, and stimulated with plate-bound anti-CD3 antibodies (i) for 30 min (E), to measure the oxidative signal (quantified as in (A)). (ii) For 1 h (F), to detect changes in CD95L expression (left panel semi quantitative PCR; right panel quantitative PCR). (iii) For 24 h (G) to assessed AICD by a drop in FCS/SSC index. Insert show T cells cotreated with or without CD95L neutralizing antibody (results were recalculated to "specific cell death"). H, Schematic diagram of TCR induced oxidative signalling.
Figure 9:
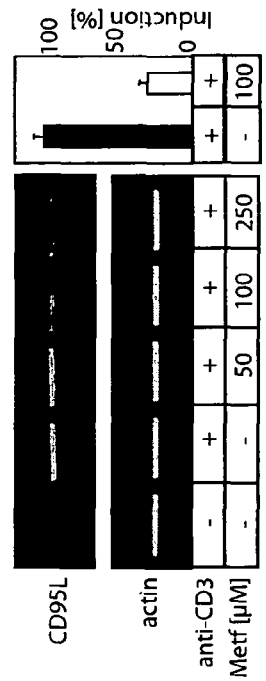
Figure 9:
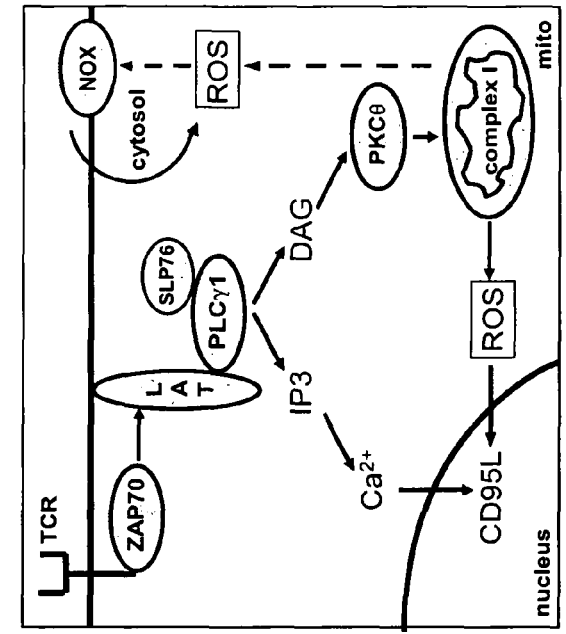
Figure 9:
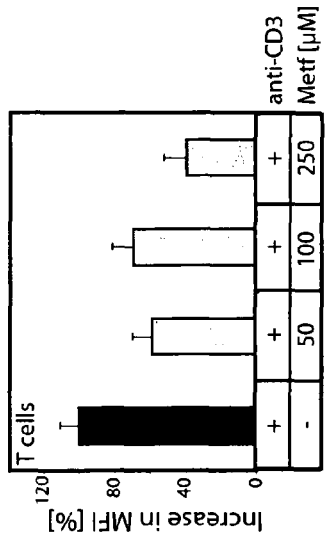
Figure 9:
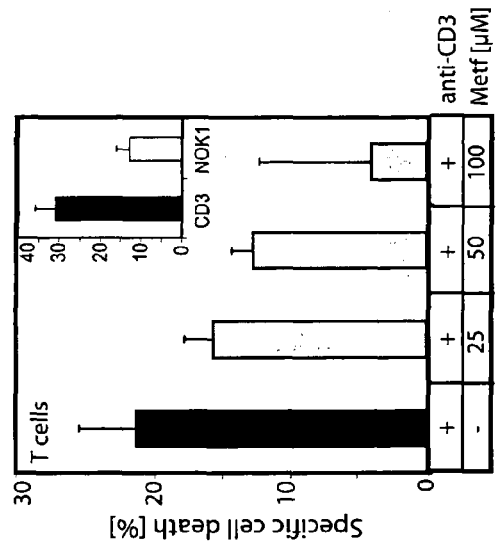
Figure 10:
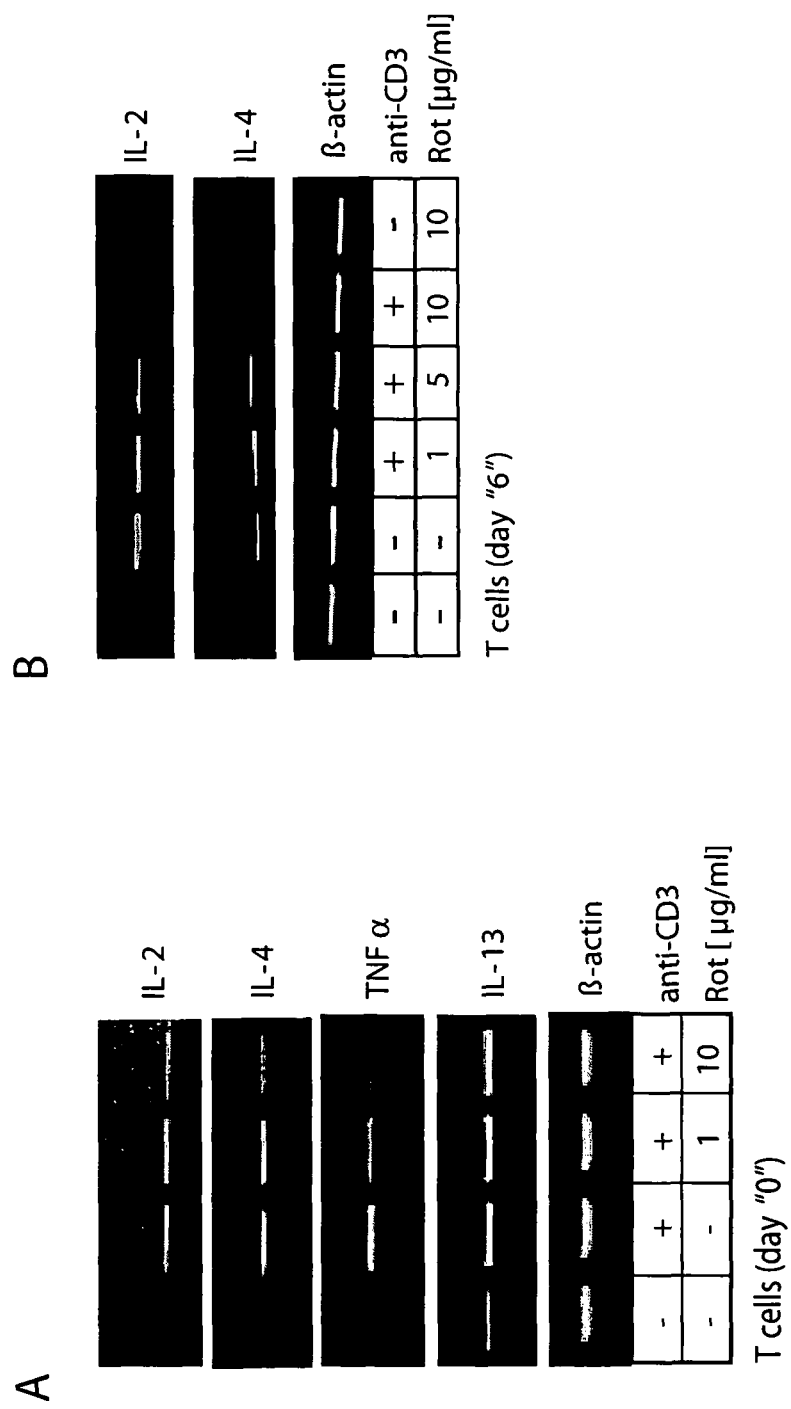
FIG. 10. A and B, Non-activated (day "0"—A) or pre-activated (day "6"—B) peripheral human T cells were pretreated with indicated amounts of rotenone for 5 min and stimulated with anti-CD3 antibodies for 1 h. Next, RNA was isolated, reverse-transcribed, and amplified using IL-2, IL-4, TNF α, IL-13 and actin-specific primers.
Figure 10:
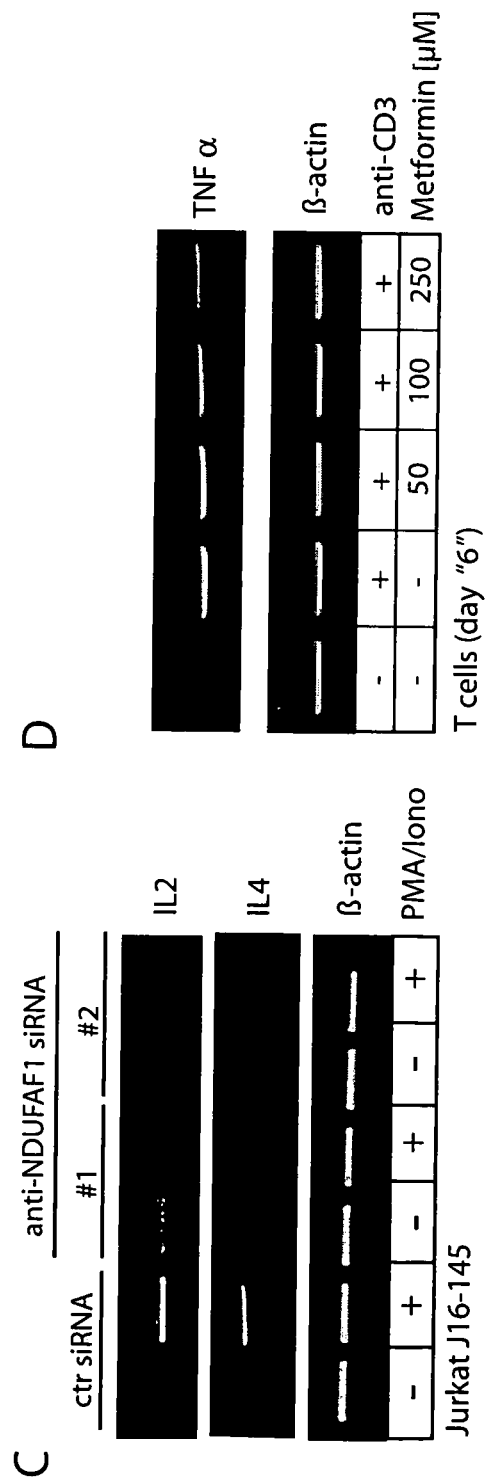

To further underline the physiological relevance of complex I derived ROS in AICD preactivated primary human T cells (day 6 T cells) were restimulated with anti-CD3 antibodies and pretreated with or without rotenone or antimycin A. The activation-induced oxidative signal (FIG. 9A) and CD95L expression (FIG. 9B) were exclusively inhibited by rotenone. In order to prove that complex I is the source of the oxidative signal, preactivated T cells (day 6 T cells) transfected with NDUFAF1 siRNA oligonucleotides (FIG. 9C) were used to measure ROS generation upon CD3 triggering. The NDUFAF1 siRNA oligonucleotides abolished activation-induced ROS generation up to 30% (FIG. 9D). In addition, we analysed the effects of metformin on primary human T cells. Metformin inhibits the anti-CD3 induced oxidative signal (FIG. 9E) and induction of CD95L expression (up to 70% inhibition) (FIG. 9F). Since AICD is mainly CD95L dependent, cell death was nearly completely inhibited by metformin (FIG. 9G). Apoptosis in primary T cells induced by direct stimulation of the CD95 receptor was not affected by metformin treatment (data not shown). Thus, the non-toxic complex I inhibitor seems to be a promising tool for treatment of diseases where deregulation of CD95L expression plays a crucial role.

Discussion

The molecular source and the signalling steps necessary for ROS production are largely unknown. Here we show for the first time that activation-induced ROS generation depends on the classical components of the TCR signalling machinery (FIG. 9H). Upon TCR stimulation Lat is phosphorylated by ZAP70 and recruits PLCγ1, which generates $IP_3$ and DAG. DAG, as well as its mimetic PMA, activates several classes of enzymes, namely PKCs, PKDs, DGKs, RasGRP and chimearins (9). However, we showed here an involvement of PKCs in activation-induced oxidative signalling. Application of BIM, a PKC-ATP binding blocker, and a specific pseudosubstrate peptide inhibited PMA- and TCR-induced ROS generation. PMA induces an oxidative signal without influencing the cytosolic $Ca^{2+}$ level (25). Therefore, it is probable that nPKCs (calcium independent) mediate activation-induced ROS generation. Despite the fact that the nPKC isoform PKCδ is involved in ROS generation in keratinocytes and myeloid leukaemia cells (39, 43), we show here that PKCθ is essential for activation-induced ROS production in T cells. Moreover, it is known that PKCθ is crucial for T cell development and activation of the transcription factors AP-1 and NF-κB (48, 59). These transcription factors are major regulators of CD95L expression (26). In addition, AP-1 as well as NF-κB are ROS sensitive (17). Thus, these data are in line with the important role of PKCθ in oxidative signalling addressed by us.

PKCs are known to activate NOX2. Recently, it has been shown that human and murine T cells express NOX2. T cells from mice deficient in these subunits displayed a reduced ROS production upon TCR stimulation (30). Here we demonstrate that NADPH oxidases participate in activation-induced ROS generation in human T cells. Comparable to murine T cells, the oxidative signal is only partially NADPH oxidase dependent (FIG. 9H). Therefore, we focused on the identification of an additional source of ROS. Mitochondria are the most prominent intracellular source of ROS production (53). It has been reported that PKCs are translocated into/to mitochondria after PMA treatment (39, 43). Here we show that upon activation PKCθ is translocated to the mitochondria and/or associated membrane structures. In addition, mitochondria translocate to the plasma membrane and the immunological synapse upon T cell activation (49). To analyse the role of mitochondria in activation-induced ROS generation in more detail we used cells transiently depleted of mtDNA, pseudo-$\rho^0$ cells (12, 36). These cells not only reveal a diminished activation-induced oxidative signal but also a reduction of AICD. Therefore, we demonstrate for the first time that expression of mitochondrial encoded proteins is a prerequisite for induction of AICD.

The ETC components are oligomeric complexes consisting of both nuclear and mtDNA-encoded subunits. The primary sites for mitochondrial ROS production by the ETC are complexes I and III (45). It has been shown that rotenone, a commonly used inhibitor of complex I, interferes with CD8$^+$ T cell function (70) and activation-induced CD95L expression (7). Nevertheless, rotenone inhibits, in addition, spindle microtubule formation and tubulin assembly leading to cell cycle arrest, disassembly of the Golgi apparatus, disturbance of the cytoskeleton and tubulin-dependent cell signalling events (4, 5, 8, 16, 32, 44, 52). Therefore, it is likely that rotenone interferes with formation of the immunological synapse and movement of mitochondria.

However, here we prove the role of complex I in activation induced ROS production, CD95L expression, and AICD via downmodulation of NDUFAF1 expression (FIG. 9H). Moreover, we exclude the participation of the other complexes of the ETC in activation-induced ROS production by the use of different inhibitors. Thus, we show here that it is indeed complex I which generates ROS and is therefore responsible for induction of CD95L expression and AICD. It is under discussion whether it is $O_2^-$ (15) or $H_2O_2$ (25) which acts as a second messenger in CD95L expression and AICD. However, complex I is known to generate $O_2^-$ into the mitochondrial matrix (65). In aqueous solutions $O_2^-$ has a half life time of less than 1 μs and is converted into $H_2O_2$ rapidly (53). MnSOD, an enzyme located the mitochondrial matrix, facilitates the conversion of $O_2^-$ into $H_2O_2$ further. Here we show that MnSOD expression and activity is enhanced upon TCR stimulation. Thus, $O_2^-$ generated by complex I is converted into $H_2O_2$ that can cross the mitochondrial membrane and acts then as a second messenger in the cytosol. Blockage of complex I via inhibitors and siRNA-mediated downmodulation of NDUFAF1 expression leads to a nearly complete block of ROS generation. Therefore, complex I activity is crucial for subsequent NADPH oxidase dependent ROS production (FIG. 9H). Recently, a similar connection between mitochondrial ROS generation and activation of NOX1 has been described in 293T cells (38). Thus, we demonstrate that ROS produced by mitochondria, despite being known as a damaging by-product of respiration, can also be released in a controlled process and serve as a second messenger.

Next, we searched for potential tools to manipulate generation of ROS at complex I and verify weather our findings have possible applications in treatment of CD95/CD95L dependent diseases. Therefore, we analysed the effect of metformin, an anti-diabetic drug (2, 3, 58) and mild inhibitor of complex I (6, 18) on AICD. Here we demonstrate that metformin inhibits activation-induced ROS production and thereby CD95L expression and AICD. It has been shown in vitro that metformin inhibits reversed electron flux towards complex I (6). Therefore, we assume that activation-induced ROS production is coupled to reversed electron transport. Importantly, metformin is a non-toxic complex I inhibitor and therefore, a potential tool to investigate diseases displaying defects in mitochondrial function combined with deregulation of CD95L expression.

AICD guards against development of autoimmunity. Thus, the pathology of a recently reported case of fatal neonatal-onset mitochondrial respiratory chain disease with manifestation of T cell immunodeficiency (51) could possibly be explained by our findings. Furthermore, multiple sclerosis (MS) is generally considered to be an inflammatory disease with a substantial autoimmune contribution. On the one hand, it was shown in a genetic screening that about 20% of MS patients revealed mutations in their mtDNA (34). It was also stated that mitochondrial complex I gene variants are associated with MS (67). On the other hand, many patients suffering from LHON (Leber's hereditary optic neuropathy) disease caused by mutations in the mitochondria-encoded subunits of complex I display symptoms of MS (33). The MS pathology in patients with mutations in genes of complex I is not understood so far, therefore, our data warrant to investigate whether CD95L expression may play a role in its development. The same applies to the T cell specific immunodeficiency disorder associated with purine nucleoside phosphorylase deficiency, which is a result of inhibition of mtDNA repair due to the accumulation of dGTP in mitochondria (1). Since CD95L plays an important role in T cell development, mitochondrial damage may be responsible for impaired thymocyte differentiation in this disease. In addition, several T cell dependent diseases are associated with enhanced ROS levels e.g. lupus erythematosus (47), rheumatoid arthritis (22), and AIDS (25), which influence T cell activation, death and homeostasis. Thus, the presented findings might have further implications for the development of non-toxic inhibitors of complex I to treat diseases where deregulation of CD95L expression or T-cell activation plays a vital role.

REFERENCES

1. Arpaia, E., P. Benveniste, A. Di Cristofano, Y. Gu, I. Dalai, S. Kelly, M. Hershfield, P. P. Pandolfi, C. M. Roifman, and 1. A. Cohen. 2000. Mitochondrial basis for immune deficiency. Evidence from purine nucleoside phosphorylase-deficient mice. J Exp Med 191:2197-208.
2. Bailey, C. J. 1992. Biguanides and NIDDM. Diabetes Care 15:755-72.
3. Bailey, C. J., and R. C. Turner. 1996. Metformin. N Engl J Med 334:574-9.
4. Barham, S. S., and B. R. Brinkley. 1976. Action of rotenone and related respiratory inhibitors on mammalian cell division. 1 Cell kinetics and biochemical aspects. Cytobios 15:85-96.
5. Barham, S. S., and B. R. Brinkley. 1976. Action of rotenone and related respiratory inhibitors on mammalian cell division. 2 Ultrastructural studies. Cytobios 15:97-109.
6. Batandier, C., B. Guigas, B. Detaille, M. Y. El-Mir, E. Fontaine, M. Rigoulet, and X. M. Leverve. 2006. The ROS production induced by a reverse-electron flux at respiratory-chain complex 1 is hampered by metformin. J Bioenerg Biomembr 38:33-42.
7. Bauer, M. K., M. Vogt, M. Los, J. Siegel, S. Wesselborg, and K. Schulze-Osthoff. 1998. Role of reactive oxygen intermediates in activation-induced CD95 (APO-1/Fas) ligand expression. J Biol Chem 273:8048-55.
8. Brinkley, B. R., S. S. Barham, S. C. Barranco, and G. M. Fuller. 1974. Rotenone inhibition of spindle microtubule assembly in mammalian cells. Exp Cell Res 85:41-6.
9. Brose, N., and C. Rosenmund. 2002. Move over protein kinase C, you've got company: alternative cellular effectors of diacylglycerol and phorbol esters. J Cell Sci 115: 4399-411.
10. Carroll, J., I. M. Fearnley, J. M. Skehel, M. J. Runswick, R. J. Shannon, J. Hirst, and J. E. Walker. 2005. The post-translational modifications of the nuclear encoded subunits of complex I from bovine heart mitochondria. Mol Cell Proteomics 4:693-9.
11. Chan, A. C., B. A. Irving, J. D. Fraser, and A. Weiss. 1991. The zeta chain is associated with a tyrosine kinase and upon T-cell antigen receptor stimulation associates with ZAP-70, a 70-kDa tyrosine phosphoprotein. Proc Natl Acad Sci USA 88:9166-70.
12. Chen, K., S. R. Thomas, A. Albano, M. P. Murphy, and J. F. Keaney, Jr. 2004. Mitochondrial function is required for hydrogen peroxide-induced growth factor receptor trans-activation and downstream signaling. J Biol Chem 279: 35079-86.
13. Chernyak, B. V., O. Y. Pletjushkina, D. S. Izyumov, K. G. Lyamzaev, and A. V. Avetisyan. 2005. Bioenergetics and death. Biochemistry (Mosc) 70:240-5.
14. Cross, A. R., and O. T. Jones. 1986. The effect of the inhibitor diphenylene iodonium on the superoxide-generating system of neutrophils. Specific labelling of a component polypeptide of the oxidase. Biochem J 237:111-6.
15. Devadas, S., L. Zaritskaya, S. G. Rhee, L. Oberley, and M. S. Williams. 2002. Discrete generation of superoxide and hydrogen peroxide by T cell receptor stimulation: selective regulation of mitogen-activated protein kinase activation and fas ligand expression. J Exp Med 195:59-70.
16. Diaz-Corrales, F. J., M. Asanuma, I. Miyazaki, K. Miyoshi, and N. Ogawa. 2005. Rotenone induces aggregation of gamma-tubulin protein and subsequent disorganization of the centrosome: relevance to formation of inclusion bodies and neurodegeneration. Neuroscience 133:117-35.
17. Droge, W. 2002. Free radicals in the physiological control of cell function. Physiol Rev 82:47-95.
18. El-Mir, M. Y., V. Nogueira, E. Fontaine, N. Averet, M. Rigoulet, and X. Leverve. 2000. Dimethylbiguanide inhibits cell respiration via an indirect effect targeted on the respiratory chain complex I. J Biol Chem 275:223-8.
19. Finco, T. S., T. Kadlecek, W. Zhang, L. E. Samelson, and A. Weiss. 1998. LAT is required for TCR-mediated activation of PLCgamma1 and the Ras pathway. Immunity 9:617-26.
20. Fridovich, I. 1970. Quantitative aspects of the production of superoxide anion radical by milk xanthine oxidase. J Biol Chem 245:4053-7.
21. Goldstone, S. D., A. D. Milligan, and N. H. Hunt. 1996. Oxidative signalling and gene expression during lymphocyte activation. Biochim Biophys Acta 1314:175-82.
22. Griffiths, H. R. 2005. ROS as signalling molecules in T cells—evidence for abnormal redox signalling in the autoimmune disease, rheumatoid arthritis. Redox Rep 10:273-80.
23. Guigas, B., D. Detaille, C. Chauvin, C. Batandier, F. De Oliveira, E. Fontaine, and X. Leverve. 2004. Metformin inhibits mitochondrial permeability transition and cell death: a pharmacological in vitro study. Biochem J 382: 877-84.
24. Gulow, K., D. Bienert, and I. G. Haas. 2002. BiP is feed-back regulated by control of protein translation efficiency. J Cell Sci 115:2443-52.
25. Gulow, K., M. Kaminski, K. Darvas, D. Suss, M. Li-Weber, and P. H. Krammer. 2005. HIV-1 Trans-Activator of Transcription Substitutes for Oxidative Signaling in Activation-Induced T Cell Death. J Immunol 174:5249-60.
26. Gulow, K., M. Kaminski, and P. Krammer. 2006. The role of CD95/CD95 Ligand Signaling in Apoptosis and Cancer. In Apoptosis and Cancer Therapy Part I. WILEY-VCH, Weinheim.
27. Halliwell, B., and J. M. Gutteridge. 1985. The importance of free radicals and catalytic metal ions in human diseases. Mol Aspects Med 8:89-193.
28. Horgan, D. J., H. Ohno, and T. P. Singer. 1968. Studies on the respiratory chain-linked reduced nicotinamide adenine dinucleotide dehydrogenase. XV. Interactions of piericidin with the mitochondrial respiratory chain. J Biol Chem 243:5967-76.
29. Irvin, B. J., B. L. Williams, A. E. Nilson, H. O. Maynor, and R. T. Abraham. 2000. Pleiotropic contributions of phospholipase C-gamma1 (PLC-gamma1) to T-cell antigen receptor-mediated signaling: reconstitution studies of a PLC-gamma1-deficient Jurkat T-cell line. Mol Cell Biol 20:9149-61.
30. Jackson, S. H., S. Devadas, J. Kwon, L. A. Pinto, and M. S. Williams. 2004. T cells express a phagocyte-type NADPH oxidase that is activated after T cell receptor stimulation. Nat Immunol 5:818-27.
31. Janssen, R., J. Smeitink, R. Smeets, and L. van Den Heuvel. 2002. CIA30 complex I assembly factor: a candidate for human complex I deficiency? Hum Genet 110: 264-70.
32. Jiang, Q., Z. Yan, and J. Feng. 2006. Activation of group III metabotropic glutamate receptors attenuates rotenone toxicity on dopaminergic neurons through a microtubule-dependent mechanism. J Neurosci 26:4318-28.
33. Kalman, B., and H. Alder. 1998. Is the mitochondrial DNA involved in determining susceptibility to multiple sclerosis? Acta Neurol Scand 98:232-7.
34. Kalman, B., S. Li, D. Chatterjee, J. O'Connor, M. R. Voehl, M. D. Brown, and H. Alder. 1999. Large scale screening of the mitochondrial DNA reveals no pathogenic mutations but a haplotype associated with multiple sclerosis in Caucasians. Acta Neurol Scand 99:16-25.

35. Keisari, Y., L. Braun, and E. Flescher. 1983. The oxidative burst and related phenomena in mouse macrophages elicited by different sterile inflammatory stimuli. Immunobiology 165:78-89.
36. King, M. P., and G. Attardi. 1989. Human cells lacking mtDNA: repopulation with exogenous mitochondria by complementation. Science 246:500-3.
37. Ku, G. M., D. Yablonski, E. Manser, L. Lim, and A. Weiss. 2001. A PAK1-PIX-PKL complex is activated by the T-cell receptor independent of Nck, Slp-76 and LAT. Embo J 20:457-65.
38. Lee, S. B., I. H. Bae, Y. S. Bae, and H. D. Um. 2006. Link between mitochondria and NADPH oxidase 1 isozyme for the sustained production of reactive oxygen species and cell death. J Biol Chem.
39. Li, L., P. S. Lorenzo, K. Bogi, P. M. Blumberg, and S. H. Yuspa. 1999. Protein kinase Cdelta targets mitochondria, alters mitochondrial membrane potential, and induces apoptosis in normal and neoplastic keratinocytes when overexpressed by an adenoviral vector. Mol Cell Biol 19:8547-58.
40. Li-Weber, M., M. Giaisi, M. K. Treiber, and P. H. Krammer. 2002. The anti-inflammatory sesquiterpene lactone parthenolide suppresses IL-4 gene expression in peripheral blood T. Eur J Immunol 32:3587-97.
41. Li-Weber, M., O. Laur, and P. H. Krammer. 1999. Novel Egr/NF-AT composite sites mediate activation of the CD95 (APO-1/Fas) ligand promoter in response to T cell stimulation. Eur J Immunol 29:3017-27.
42. Luetjens, C. M., N. T. Bui, B. Sengpiel, G. Munstermann, M. Poppe, A. J. Krohn, E. Bauerbach, J. Krieglstein, and J. H. Prehn. 2000. Delayed mitochondrial dysfunction in excitotoxic neuron death: cytochrome c release and a secondary increase in superoxide production. J Neurosci 20:5715-23.
43. Majumder, P. K., P. Pandey, X. Sun, K. Cheng, R. Datta, S. Saxena, S. Kharbanda, and D. Kufe. 2000. Mitochondrial translocation of protein kinase C delta in phorbol ester-induced cytochrome c release and apoptosis. J Biol Chem 275:21793-6.
44. Marshall, L. E., and R. H. Himes. 1978. Rotenone inhibition of tubulin self-assembly. Biochim Biophys Acta 543:590-4.
45. McLennan, H. R., and M. Degli Esposti. 2000. The contribution of mitochondrial respiratory complexes to the production of reactive oxygen species. J Bioenerg Biomembr 32:153-62.
46. Nathan, C. F., and R. K. Root. 1977. Hydrogen peroxide release from mouse peritoneal macrophages: dependence on sequential activation and triggering. J Exp Med 146:1648-62.
47. Perl, A., G. Nagy, P. Gergely, F. Puskas, Y. Qian, and K. Banki. 2004. Apoptosis and mitochondrial dysfunction in lymphocytes of patients with systemic lupus erythematosus. Methods Mol Med 102:87-114.
48. Pfeifhofer, C., K. Kofler, T. Gruber, N. G. Tabrizi, C. Lutz, K. Maly, M. Leitges, and G. Baier. 2003. Protein kinase C theta affects Ca2+ mobilization and NFAT cell activation in primary mouse T cells. J Exp Med 197:1525-35.
49. Quintana, A., E. C. Schwarz, C. Schwindling, P. Lipp, L. Kaestner, and M. Hoth. 2006. Sustained activity of CRAC channels requires translocation of mitochondria to the plasma membrane. J Biol Chem.
50. Rashba-Step, J., N. J. Turro, and A. I. Cederbaum. 1993. Increased NADPH- and NADH-dependent production of superoxide and hydroxyl radical by microsomes after chronic ethanol treatment. Arch Biochem Biophys 300:401-8.
51. Reichenbach, J., R. Schubert, R. Horvath, J. Petersen, N. Futterer, E. Malle, A. Stumpf, B. R. Gebhardt, U. Koehl, B. Schraven, and S. Zielen. 2006. Fatal neonatal-onset mitochondrial respiratory chain disease with T cell immunodeficiency. Pediatr Res 60:321-6.
52. Ren, Y., W. Liu, H. Jiang, Q. Jiang, and J. Feng. 2005. Selective vulnerability of dopaminergic neurons to microtubule depolymerization. J Biol Chem 280:34105-12.
53. Reth, M. 2002. Hydrogen peroxide as second messenger in lymphocyte activation. Nat Immunol 3:1129-34.
54. Rosen, G. M., and B. A. Freeman. 1984. Detection of superoxide generated by endothelial cells. Proc Natl Acad Sci USA 81:7269-73.
55. Sanders, S. A., R. Eisenthal, and R. Harrison. 1997. NADH oxidase activity of human xanthine oxidoreductase—generation of superoxide anion. Eur J Biochem 245:541-8.
56. Sies, H. 1977. Peroxisomal enzymes and oxygen metabolism in liver. Adv Exp Med Biol 78:51-60.
57. Stuehr, D. J., O. A. Fasehun, N. S. Kwon, S. S. Gross, J. A. Gonzalez, R. Levi, and C. F. Nathan. 1991. Inhibition of macrophage and endothelial cell nitric oxide synthase by diphenyleneiodonium and its analogs. Faseb J 5:98-103.
58. Stumvoll, M., N. Nurjhan, G. Perriello, G. Dailey, and J. E. Gerich. 1995. Metabolic effects of metformin in non-insulin-dependent diabetes mellitus. N Engl J Med 333:550-4.
59. Sun, Z., C. W. Arendt, W. Ellmeier, E. M. Schaeffer, M. J. Sunshine, L. Gandhi, J. Annes, D. Petrzilka, A. Kupfer, P. L. Schwartzberg, and D. R. Littman. 2000. PKC-theta is required for TCR-induced NF-kappaB activation in mature but not immature T lymphocytes. Nature 404:402-7.
60. t Hart, B. A., J. M. Simons, S. Knaan-Shanzer, N. P. Bakker, and R. P. Labadie. 1990. Antiarthritic activity of the newly developed neutrophil oxidative burst antagonist apocynin. Free Radic Biol Med 9:127-31.
61. Tew, D. G. 1993. Inhibition of cytochrome P450 reductase by the diphenyliodonium cation. Kinetic analysis and covalent modifications. Biochemistry 32:10209-15.
62. Trauth, B. C., C. Klas, A. M. Peters, S. Matzku, P. Moller, W. Falk, K. M. Debatin, and P. H. Krammer. 1989. Monoclonal antibody-mediated tumor regression by induction of apoptosis. Science 245:301-5.
63. Turrens, J. F., B. A. Freeman, J. G. Levitt, and J. D. Crapo. 1982. The effect of hyperoxia on superoxide production by lung submitochondrial particles. Arch Biochem Biophys 217:401-10.
64. Villunger, A., N. Ghaffari-Tabrizi, I. Tinhofer, N. Krumbock, B. Bauer, T. Schneider, S. Kasibhatla, R. Greil, G. Baier-Bitterlich, F. Uberall, D. R. Green, and G. Baier. 1999. Synergistic action of protein kinase C theta and calcineurin is sufficient for Fas ligand expression and induction of a crmA-sensitive apoptosis pathway in Jurkat T cells. Eur J Immunol 29:3549-61.
65. Vinogradov, A. D., and V. G. Grivennikova. 2005. Generation of superoxide-radical by the NADH:ubiquinone oxidoreductase of heart mitochondria. Biochemistry (Mosc) 70:120-7.
66. Vogel, R. O., R. J. Janssen, C. Ugalde, M. Grovenstein, R. J. Huijbens, H. J. Visch, L. P. van den Heuvel, P. H. Willems, M. Zeviani, J. A. Smeitink, and L. G. Nijtmans. 2005. Human mitochondrial complex I assembly is mediated by NDUFAF1. Febs J 272:5317-26.

67. Vyshkina, T., I. Banisor, Y. Y. Shugart, T. P. Leist, and B. Kalman. 2005. Genetic variants of Complex I in multiple sclerosis. J Neurol Sci 228:55-64.
68. Williams, B. L., K. L. Schreiber, W. Zhang, R. L. Wange, L. E. Samelson, P. J. Leibson, and R. T. Abraham. 1998. Genetic evidence for differential coupling of Syk family kinases to the T-cell receptor: reconstitution studies in a ZAP-70-deficient Jurkat T-cell line. Mol Cell Biol 18:1388-99.
69. Williamson, J. R. 1986. Role of inositol lipid breakdown in the generation of intracellular signals. State of the art lecture. Hypertension 8:II140-56.
70. Yi, J. S., B. C. Holbrook, R. D. Michalek, N. G. Laniewski, and J. M. Grayson. 2006. Electron transport complex I is required for CD8+ T cell function. J Immunol 177:852-62.

The invention claimed is:

1. A method of treating a patient having a T-cell mediated inflammatory disease, the method comprising administering to said patient a therapeutically effective amount of a compound which inhibits complex I-mediated ROS production.

2. The method according to claim 1, wherein the compound is capable of inhibiting reversed electron flux.

3. The method according to claim 2, wherein the compound belongs to the class of biguanides.

4. The method of claim 3, wherein the biguanide is metformin or a pharmaceutically acceptable salt thereof.

5. The method according to claim 1, wherein the compound is capable of destabilizing complex I.

6. The method according to claim 5, wherein the compound comprises a siRNA molecule wherein the siRNA molecule interferes with the expression of NDUFAF1.

7. The method according to claim 1, wherein the T-cell mediated inflammatory disease is selected from the group consisting of graft-versus-host disease, lupus erythematosis, sepsis, asthma, psoriasis, atopical dermatitis, and multiple sclerosis.

8. A medicament against a T-cell mediated inflammatory disease, the medicament containing a therapeutically effective amount of a combination of compounds which inhibit complex I-mediated ROS production.

9. The medicament of claim 8, wherein the compounds which inhibit complex I-mediated ROS production are metformin or a pharmaceutically acceptable salt thereof and a compound which is capable of destabilizing complex I.

* * * * *